US009155652B2

(12) United States Patent
Peyman

(10) Patent No.: US 9,155,652 B2
(45) Date of Patent: Oct. 13, 2015

(54) METHOD FOR LASER CORRECTION OF REFRACTIVE ERRORS OF AN EYE WITH A THIN CORNEA

(76) Inventor: Gholam A. Peyman, Sun City, AZ (US)

(*) Notice: Subject to any disclaimer, the term of this patent is extended or adjusted under 35 U.S.C. 154(b) by 162 days.

(21) Appl. No.: 12/770,011

(22) Filed: Apr. 29, 2010

(65) Prior Publication Data

US 2010/0210996 A1     Aug. 19, 2010

Related U.S. Application Data

(63) Continuation-in-part of application No. 12/608,249, filed on Oct. 29, 2009, which is a continuation-in-part of application No. 11/676,793, filed on Feb. 20, 2007, now abandoned, which is a continuation-in-part of application No. 11/446,065, filed on Jun. 1, 2006, now abandoned, which is a continuation-in-part of application No. 11/070,659, filed on Mar. 2, 2005, now abandoned, which is a continuation-in-part of application No. 09/986,141, filed on Nov. 7, 2001, now Pat. No. 6,918,904.

(51) Int. Cl.
*A61F 9/008* (2006.01)
*A61F 7/00* (2006.01)
*A61F 9/009* (2006.01)

(52) U.S. Cl.
CPC ............ *A61F 7/007* (2013.01); *A61F 9/00804* (2013.01); *A61F 9/00827* (2013.01); *A61F 9/008* (2013.01); *A61F 9/009* (2013.01); *A61F 9/00812* (2013.01); *A61F 9/00821* (2013.01); *A61F 2007/0004* (2013.01); *A61F 2007/0054* (2013.01); *A61F 2009/0088* (2013.01); *A61F 2009/00872* (2013.01); *A61F 2009/00897* (2013.01)

(58) Field of Classification Search
CPC ....... A61F 9/007; A61F 9/0079; A61F 9/008; A61F 9/00804; A61F 9/00812; A61F 9/00821; A61F 9/00827; A61F 9/009; A61F 2009/00872; A61F 2009/00893; A61M 2210/0612
USPC ........................... 606/4–6, 10–12, 27; 604/20
See application file for complete search history.

(56) References Cited

U.S. PATENT DOCUMENTS 4,665,913 A * 5/1987 L'Esperance, Jr. ............... 606/5
4,718,418 A    1/1988 L'Esperance, Jr.
(Continued)

FOREIGN PATENT DOCUMENTS

WO     WO 01/58495     *   8/2001 ................. 606/4

OTHER PUBLICATIONS

Wollensak et al; "Riboflavin/Ultraviolet-A-induced Collagen Crosslinking for the Treatment of Keratoconus"; Am J Ophthalmol; vol. 135, No. 5, May 2003; pp. 620-627.*
(Continued)

*Primary Examiner* — David Shay
(74) *Attorney, Agent, or Firm* — The Law Office of Patrick F. O'Reilly, III, LLC

(57) ABSTRACT

The present invention relates to a method of altering the refractive properties of the eye, the method including applying a substance to a cornea of an eye, the substance configured to facilitate cross linking of the cornea, irradiating the cornea so as to activate cross linkers in the cornea, and altering the cornea so as to change the refractive properties of the eye.

4 Claims, 21 Drawing Sheets

(56) References Cited

U.S. PATENT DOCUMENTS

| | | | |
|---|---|---|---|
| 4,840,175 A | | 6/1989 | Peyman |
| 4,903,695 A | * | 2/1990 | Warner et al. ............ 606/5 |
| 4,994,058 A | | 2/1991 | Raven et al. |
| 5,171,318 A | * | 12/1992 | Gibson et al. ............ 623/5.16 |
| 5,336,261 A | | 8/1994 | Barrett et al. |
| 5,964,748 A | * | 10/1999 | Peyman ............ 606/5 |
| 6,197,019 B1 | | 3/2001 | Peyman |
| 6,537,545 B1 | * | 3/2003 | Karageozian et al. ........ 607/88 |
| 7,001,374 B2 | * | 2/2006 | Peyman ............ 606/5 |
| 7,004,902 B2 | * | 2/2006 | Luce ............ 600/398 |
| 7,044,945 B2 | * | 5/2006 | Sand ............ 606/12 |
| 2007/0135754 A1 | * | 6/2007 | Akiyama et al. ............ 604/20 |
| 2009/0171305 A1 | * | 7/2009 | El Hage ............ 604/294 |

OTHER PUBLICATIONS

J. I. Barraquer, "Keratomileusis and Keratophakia for the Correction of Congenital Hypermetropia and Aphakia", Bulletins et Memoires de la Societe Francaise D'Ophthalmologie, vol. 95, pp. 380-390 (1984).

M. A. Bamashmus, M. F. Saleh, M. A. Awadalla, "Reasons for Not Performing Keratorefractive Surgery in Patients Seeking Refractive Surgery in a Hospital-Based Cohort in Yemen", Middle East Afr J Ophthalmol, Oct.-Dec. 2010; 17(4): pp. 349-353.

* cited by examiner

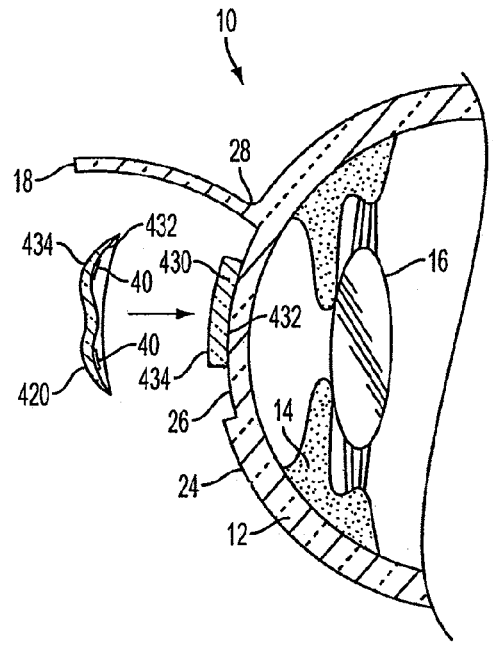 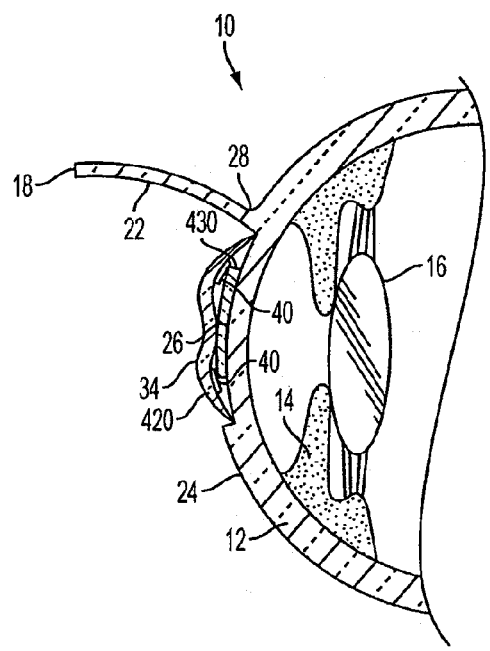
FIG. 17  FIG. 18
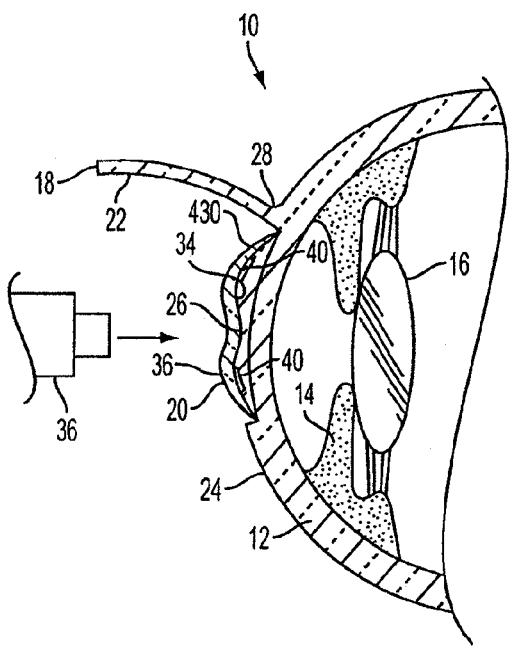 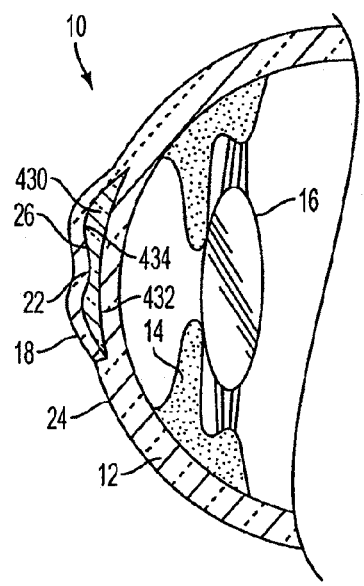
FIG. 19  FIG. 20

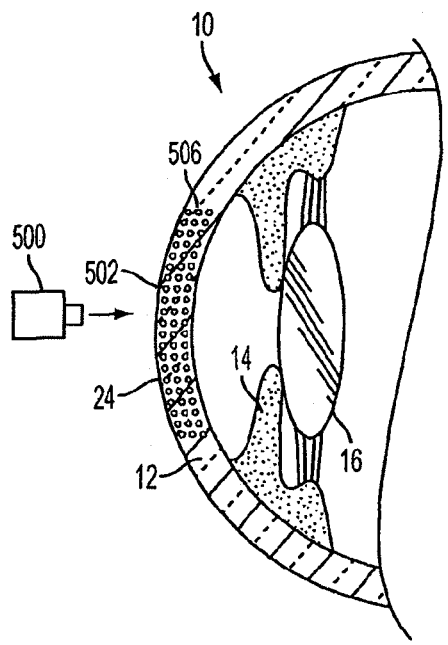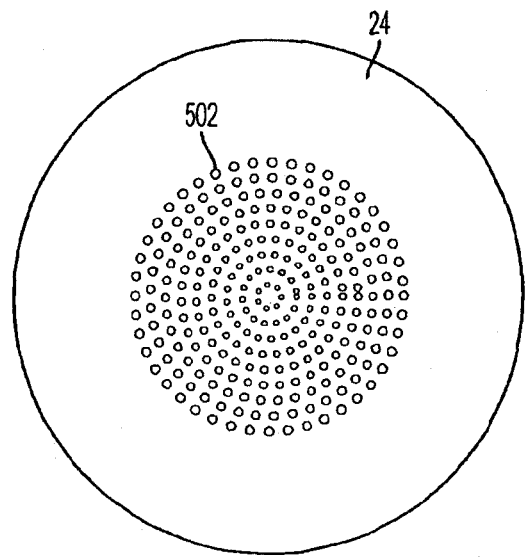
FIG. 21  FIG. 22
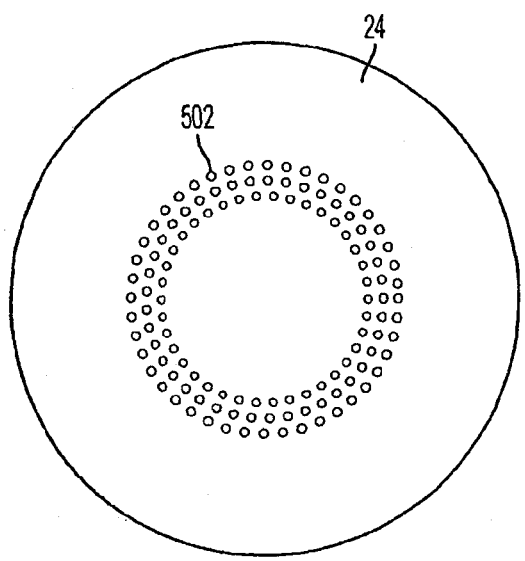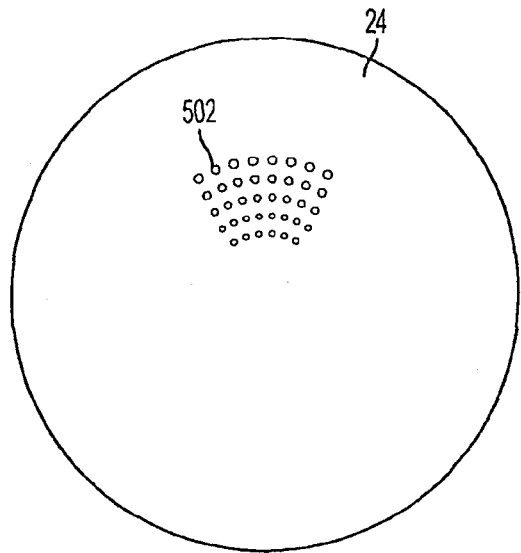
FIG. 23  FIG. 24

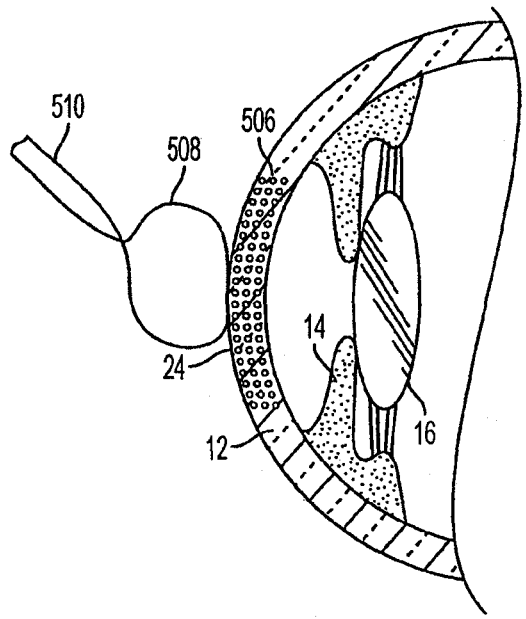 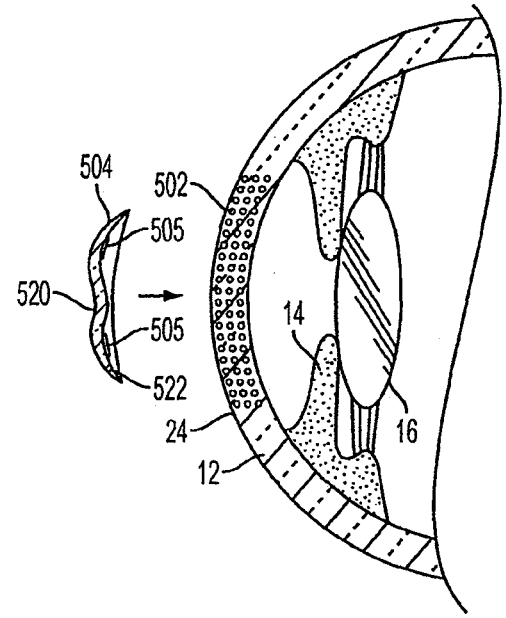
FIG. 25  FIG. 26
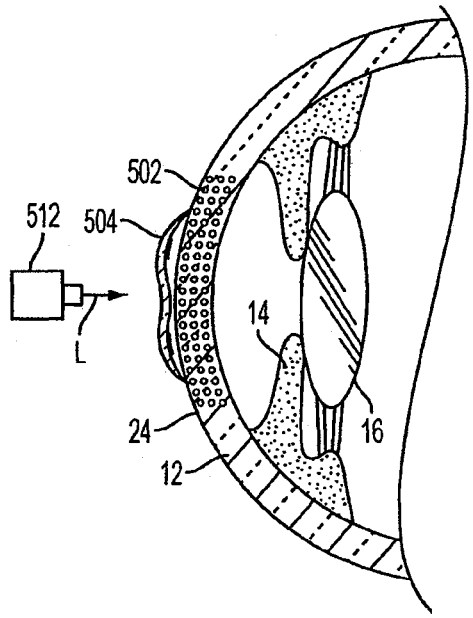 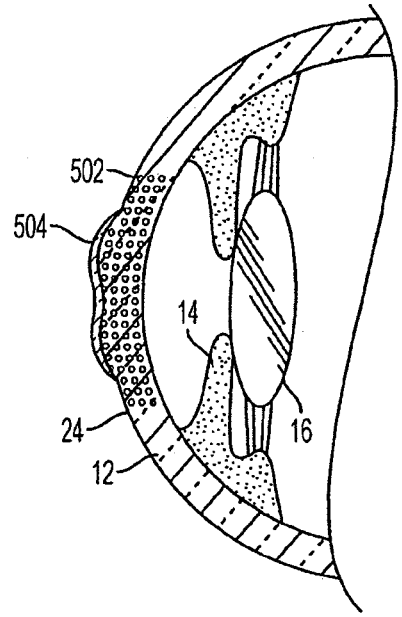
FIG. 27  FIG. 28

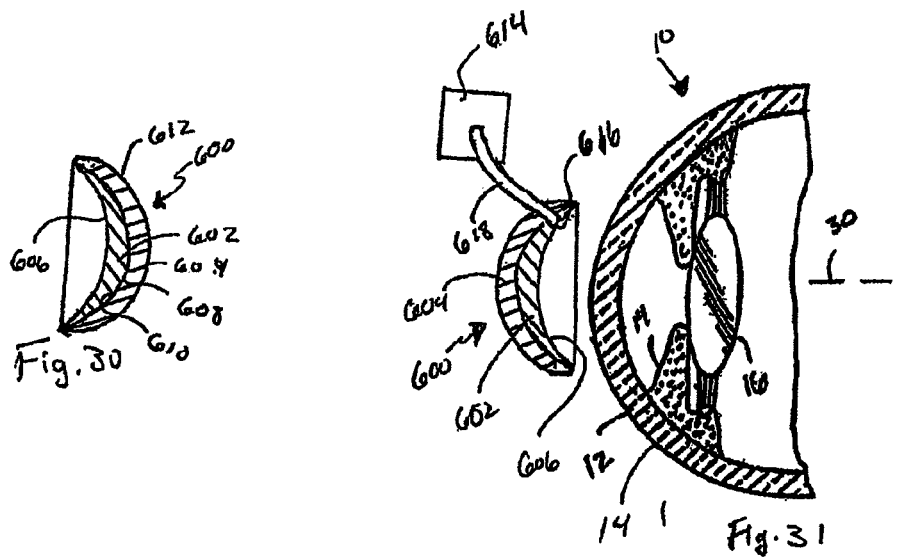
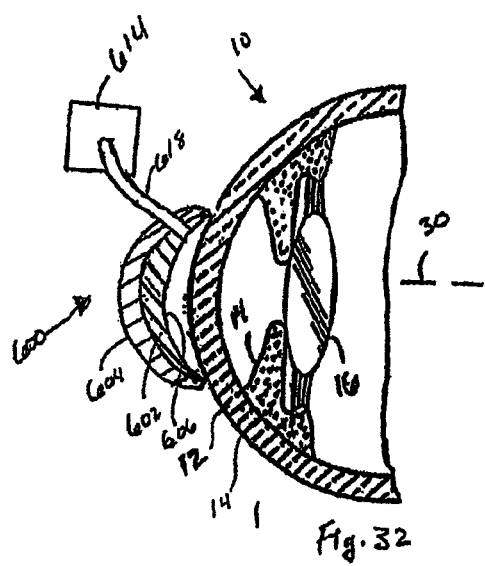

METHOD FOR LASER CORRECTION OF REFRACTIVE ERRORS OF AN EYE WITH A THIN CORNEA

RELATED APPLICATIONS

This application is a continuation-in-part of U.S. patent application Ser. No. 12/608,249, filed Oct. 29, 2009, entitled "Method for Prevention of Rejection and Severe Encapsulation of a Supportive or Functioning Implant", which is a continuation-in-part of U.S. patent application Ser. No. 11/676,793 filed Feb. 20, 2007 now abandoned, entitled "Method and System for Altering the Refractive Properties of the Eye", which is a continuation-in-part of U.S. patent application Ser. No. 11/446,065, filed Jun. 1, 2006 now abandoned, entitled "Device and Method for Reshaping the Cornea", which is a continuation-in-part of application is a continuation-in-part of U.S. patent application Ser. No. 11/070,659, filed Mar. 2, 2005 now abandoned, entitled "Device and Method for Reshaping the Cornea", which is a continuation-in-part of U.S. patent application Ser. No. 09/986,141, filed Nov. 7, 2001 now U.S. Pat. No. 6,918,904, entitled "Method of Reshaping the Cornea by Controlled Thermal Delivery", the entire contents of each of which are incorporated herein by reference.

BACKGROUND

A normal emetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused behind the retina.

An eye suffering from astigmatism has a defect in the lens or shape of the cornea. Therefore, an astigmatic eye is incapable of sharply focusing images on the retina.

Optical methods are known which involve the placement of lenses in front of the eye, for example, in the form of eyeglasses or contact lenses, to correct vision disorders. A common method of correcting myopia is to place a "minus" or concave lens in front of the eye to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. The concave, convex or other shaped lenses are typically configured in the form of glasses or contact lenses.

Although these optical methods can be used to correct vision in eyes suffering from low myopia, or in eyes suffering from hypermetropic, hyperopic or astigmatic conditions which are not very severe, these methods are ineffective in correcting vision in eyes suffering from severe forms of ametropia.

However, surgical techniques exist for correcting these more severe forms of ametropia to a certain degree. For example, in a technique known as myopic keratomileusis, a microkeratome is used to cut away a portion of the front of the live cornea from the main section of the live cornea. The cut portion of the cornea is frozen and placed in a cryolathe where it is cut and reshaped. Altering the shape of the cut portion of the cornea changes the refractive power of this cut portion, which thus affects the location at which light entering the cut portion of the cornea is focused. The reshaped cut portion of the cornea is then thawed and reattached to the main portion of the live cornea. Hence, it is intended that the reshaped cornea will change the position at which the light entering the eye through the cut portion is focused, so that hopefully the light is focused directly on the retina, thus remedying the ametropic condition.

The myopic keratomileusis technique is known to be effective in curing myopic conditions within a high range. However, the technique is impractical because it employs very complicated and time consuming freezing, cutting and thawing processes.

Keratophakia is another known surgical technique for correcting severe ametropic conditions of the eye by altering the shape of the eye's cornea. In this technique an artificial, organic or synthetic lens is implanted inside the cornea to thereby alter the shape of the cornea and thus change its refractive power. Accordingly, as with the myopic keratomileusis technique, it is desirable that the shape of the cornea be altered to a degree that allows light entering the eye to be focused correctly on the retina.

However, the keratophakia technique is relatively impractical, complicated, and expensive because it requires manufacturing or cutting a special lens prior to its insertion into the cornea. Hence, a surgeon is required to either maintain an assortment of many differently shaped lenses, or alternatively, must have access to expensive equipment, such as a cyrolathe, which can be used to cut the lens prior to insertion into the cornea.

Examples of known techniques for modifying corneal curvature, such as those discussed above, are described in U.S. Pat. No. 4,994,058 to Raven et al., U.S. Pat. No. 4,718,418 to L'Esperance, U.S. Pat. No. 5,336,261 to Barrett et al., and a publication by Jose I. Barraquer, M.D. entitled "Keratomileusis and Keratophakia in the Surgical Correction of Aphakia". The entire contents of each of these patents are incorporated herein by reference.

Surgical techniques involving the use of ultraviolet and shorter wavelength lasers to modify the shape of the cornea also are known. For example, excimer lasers, such as those described in U.S. Pat. No. 4,840,175 to Peyman, which emit pulsed ultraviolet radiation, can be used to decompose or photoablate tissue in the live cornea so as to reshape the cornea.

Specifically, a laser surgical technique known as laser in situ keratomileusis (LASIK) has been previously developed by the present inventor. In this technique, a portion of the front of a live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150-180 microns deep. The cut portion is then reattached over the ablated portion of the cornea and assumes a shape conforming to that of the ablated portion.

However, because only a certain amount of cornea can be ablated without the remaining cornea becoming unstable or experiencing outwardbulging (eklasia), this technique is not especially effective in correcting very high myopia. That is, a typical live cornea is on average about 500 microns thick. The laser ablation technique requires that at least about 200 microns of the corneal stroma remain after the ablation is completed so that instability and outwardbulging does not occur. Hence, this method typically cannot be effectively used to correct high myopia of greater than 15 diopters because, in order to reshape the cornea to the degree necessary to alter its refractive power to sufficiently correct the focusing of the eye, too much of the cornea would need to be ablated.

Additionally, the cornea can be modified using thermal coagulation. In thermal coagulation, electrodes of varying shapes are applied to the cornea in a predetermined pattern. The electrodes emit a radio frequency wave or laser light, thereby heating the surface of the cornea. Once the surface of the cornea is heated it tends to shrink, the shrinking of the cornea changes the refractive properties of the eye. In these methods, the thermal temperature generally rises in the surface of the cornea and in the deeper tissue above the coagulation threshold, producing clinical appearance of a gray to white response in the cornea, or protein detanurization. Furthermore, since the cornea can generally only be shrunk in response to thermal coagulation, this method is exclusively used for presbyopic and hyperopic correction of refractive errors.

Therefore, it is apparent that a need therefore exists for improved methods for further modifying the cornea to better correct ametropic conditions.

SUMMARY

The present invention relates to a method of altering the refractive properties of the eye, the method including applying a substance to a cornea of an eye, the substance configured to facilitate cross linking of the cornea, irradiating the cornea so as to activate cross linkers in the cornea, and altering the cornea so as to change the refractive properties of the eye.

The present invention also relates to a method of altering the refractive properties of the eye, the method comprising applying a substance to a cornea of an eye, the substance configured to facilitate cross linking of the cornea, irradiating the cornea so as to activate cross linkers in the cornea, forming a flap in the cornea, ablating a portion of the cornea under the flap using an excimer laser so as to change the refractive properties of the eye, and replacing the flap over the ablated portion of the cornea.

Additional features and advantages are described herein, and will be apparent from, the following Detailed Description and the figures.

BRIEF DESCRIPTION OF THE FIGURES

Referring to the drawings which form a part of this disclosure:

FIG. 17 is a side elevational view in cross section of the eye of FIG. 2 with a inlay positioned on the exposed surface of the cornea and with a reshaping device having a predetermined shape for correcting myopia proximate to the inlay;

FIG. 18 is a side elevational view in cross section of the eye of FIG. 17 with the reshaping device immediately adjacent the inlay;

FIG. 19 is a side elevational view in cross section of the eye of FIG. 18 with a laser irradiating the lens to soften the inlay with the softened portion of the inlay conforming to the internal shape of the lens;

FIG. 20 is a side elevational view in cross section of the eye of FIG. 19 with the lens removed and the flap repositioned over the reformed inlay;

FIG. 21 is a side elevational view in cross section of the eye of FIG. 1 with multiple cavities formed in the cornea via an ultra short pulse laser;

FIG. 22 is a front view of the eye of FIG. 21 showing the multiple cavities forming a substantially circular pattern;

FIG. 23 is a front view of an eye having multiple cavities formed using an ultra short pulse laser as shown in FIG. 21, the cavities forming a substantially ring-shaped configuration;

FIG. 24 is a front view of an eye having multiple cavities formed using an ultra short pulse laser as shown in FIG. 21, the cavities formed in an area offset from the main optical axis;

FIG. 25 is a side elevational view in cross section of the eye of FIG. 21 with a device applying a photosensitizer to the surface of the cornea;

FIG. 26 is a side elevational view in cross section of the eye of FIG. 25 with a reshaping device proximate to the external surface of the cornea;

FIG. 27 is a side elevational view in cross section of the eye of FIG. 26 with the reshaping device immediately adjacent the external corneal surface and a laser heating the cornea;

FIG. 28 is a side elevational view in cross section of the eye of FIG. 27 showing the cornea reshaped to conform to the predetermined shape of the reshaping device;

FIG. 30 is a side view in section of a device according to another embodiment of the present invention;

FIG. 31 is a side view in section of a device according to another embodiment of the present invention proximate to the surface of the cornea;

FIG. 32 is a side view in section of the device of FIG. 31 immediately adjacent the surface of the cornea;

DETAILED DESCRIPTION

Figure 1:
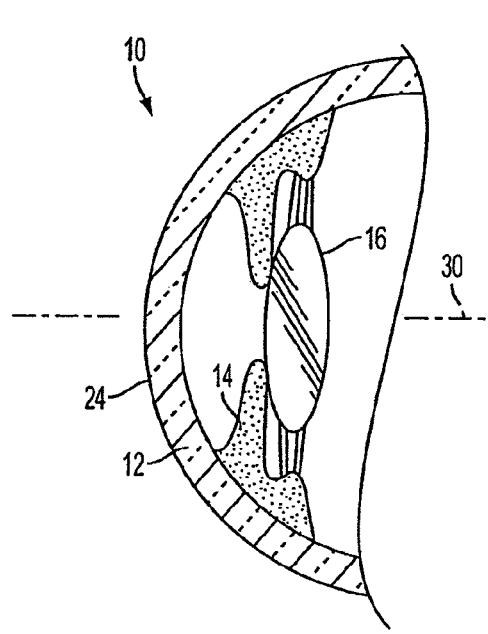
FIG. 1 is a side elevational view in cross section taken through the center of an eye showing the cornea, pupil and lens.

FIG. 1 is a side elevational view in cross section taken through the center of an eye 10, which includes a cornea 12, a pupil 14 and a lens 16. If the cornea 12 and lens 16 do not cooperatively focus light correctly on the retina (not shown) of the eye to thus provide adequate vision, the curvature of the cornea can be modified to correct the refractive power of the cornea and thus correct the manner in which the light is focused with respect to the retina.

As seen in FIGS. 1-7, the refractive properties of the eye can be modified or altered by forming a flap 18 in the surface 12 of the cornea, preferably by placing a reshaping device 20 having a predetermined shape on the surface 12 of the cornea, heating the reshaping device and in turn heating the surface of the cornea. However, it is noted that the cornea can be heated by any means suitable, such as directly by a laser or chemically or any other method that would allow heating the cornea to the proper temperature. Heating the cornea to the predetermined temperature causes the corneal stroma to cross link and have a gel-like or gelatinous consistency. The gelatinous corneal portion then can flow and reform to take the form of the interior surface 32 of the reshaping device, thus changing the refractive properties of the cornea and the eye.

To begin, the refractive error in the eye is measured using wavefront technology, as is known to one of ordinary skill in the art. The refractive error measurements are used to determine the appropriate shape of lens or contact 20 to best correct the error in the patient's cornea. Preferably, the lens 20 is manufactured or shaped prior to the use of the wavefront technology and is stored in a sterilized manner until that specific lens shape or size is needed. However, the information received during the measurements from the wavefront technology can be used to form the lens using a cryolathe, or any other desired system or machine.

Figure 2:
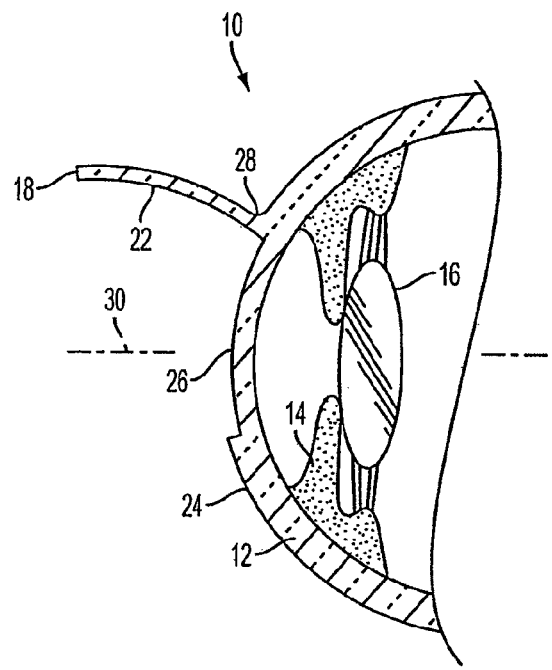
FIG. 2 is a side elevational view in cross section of the eye of FIG. 1 with a flap formed in the surface of the cornea.

In one embodiment, a flap or portion 18 can be formed in the surface 24 of the cornea 12, as seen in FIG. 2. The flap may be formed in the stromal layer of the cornea, but does not necessarily need to be formed in the stromal layer and can be formed in any desired portion of the cornea, such as the epithelium or any other portion desired. The flap may be formed be any means desired, such as with a knife, microkeratome, or with a laser. An internal area of the cornea is separated into first and second substantially circular shaped internal surfaces 22 and 26, respectively, to form the circular shaped corneal flap 18. First internal surface 22 faces in a posterior direction of cornea 12 and the second internal surface 26 faces in anterior direction of the cornea 12. The flap 18 can have a uniform thickness of about 10-250 microns, and preferably about 80-100 microns, but can be any suitable thickness. If the flap embodiment is used, a portion 28 of flap 18 preferably remains attached to the cornea by an area at the periphery of the flap. However, the flap can be any suitable configuration, such as a flap attached to the cornea at a location other than at the periphery or a flap that is not attached to the cornea at all. Additionally, the flap may be shaped or sized as desired and does not need to be circular.

The flap is moved or pivoted about portion 28 using any device known in the art, such as a spatula or microforceps or any other device, to expose the first and second corneal surfaces 22 and 26, respectively. The flap preferably exposes a portion of the corneal surface that intersects the main optical axis 30 and allows uninhibited access thereto.

Figure 4:
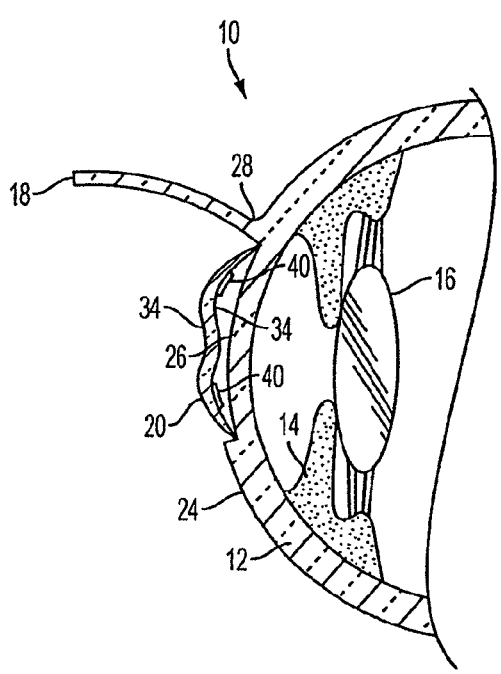
FIG. 4 is a side elevational view in cross section of the eye of FIG. 3 with the reshaping device immediately adjacent and overlying the exposed surface of the cornea.

Lens or mold 20 can then be positioned adjacent and overlying the surface 22 of the cornea, as seen in FIG. 4. However, it is noted that the lens does not necessarily need to be positioned adjacent a surface exposed by a flap and may be positioned on the external surface 24 of the cornea 12, as described below, or the second internal surface 26.

Lens 20 is preferably any metal that can absorb heat and transmit and distribute heat throughout the lens in a uniform or substantially uniform manner. However, the lens does not necessarily need to be metal and can be any synthetic or semi-synthetic material, such as plastic or any polymer or any material that has pigmentation that would allow the lens to absorb the heat from the laser and transmit and distribute the heat uniformly throughout the lens.

Additionally, lens 20 is substantially circular and has a first or inner side or surface 32 and a second or outer side or surface 34 and preferably has a substantially concave shape. The lens preferably has a predetermined shaped, or more specifically, the first surface 32 preferably has a predetermined shape that would be the proper shape of the surface 26 of the cornea plus the flap 18 to focus light onto the retina. In other words, if the interior of the cornea were the shape of the interior surface of the lens the patient would be able to have 20/20 vision or better.

FIGS. 1-7 show the correction of myopic error using a concave lens 20. However, the lens can be formed such as lens 120, shown in FIGS. 8-12 and discussed below, for correction of hyperopic error or any other shape desired for the correction of astigmatic error, presbyopia or any other error.

Figures 5, 6:
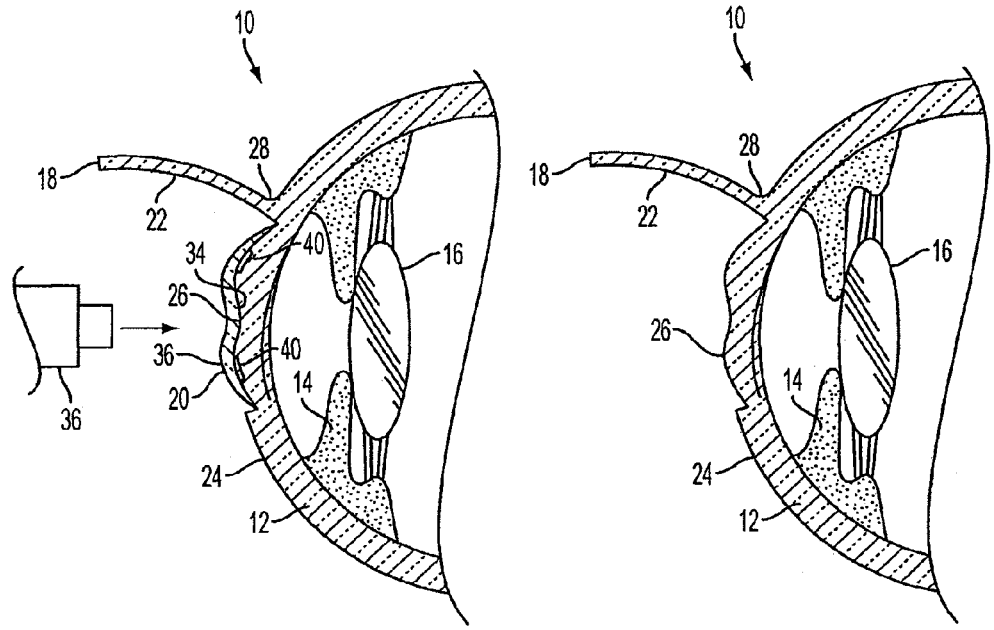
FIG. 5 is a side elevational view in cross section of the eye of FIG. 4 with a laser irradiating the reshaping device to cross link the cornea with the cross linked portion of the cornea conforming to the internal shape of the reshaping device.
FIG. 6 is a side elevational view in cross section of the eye of FIG. 5 with the reshaping device removed and the cornea maintaining its reformed shape.

Once the reshaping device is positioned immediately adjacent a surface of the cornea 12, a heating device is applied or administered to the reshaping device 20, which in turn transfers the heat to the surface of the cornea. Preferably as seen in FIG. 5, a laser 36 is aimed and fired or directed, so that the light emitted form the laser or the laser beam L is absorbed by the reshaping device 20 and then absorbed by or transferred to the cornea. Preferably, the laser beam is in the infrared portion of the electromagnetic spectrum, such as light supplied by a Nd-Yag laser at 1.32 µm, a Holmium laser at 2.2 µm or a Erb-Yag laser at 2.9 µm, or any other laser light wave length that is absorbed by water. For example, the laser light can be from a $CO_2$ laser or a visible light laser, such as an argon laser. Additionally, the reshaping device can be heated by any means suitable, such as microwaves.

The laser beam preferably heats the lens so that the inner surface of the reshaping device is about or below 60.degree. Celsius (140.degree. F.), which in turn heats the corneal surface (such as the stroma or the external surface of the cornea) to about the same temperature, thereby cross linking the cornea. The reshaping device inner surface temperature can be constantly controlled or measured, for example, using one or multiple thermal couples 40 on the inner surface of the reshaping device. The thermal couples are linked to a computer control system (not shown) using any method known in the art, such as direct electrical connection or wires or a wireless system. The computer control system monitors (or enables a user to monitor) the temperature and controls (or enables a user to control) the laser to change the temperature of the reshaping device. The computer can maintain a precise constant temperature, increase temperature or decrease temperature as desired, and at any rate desired. This computer control system, along with the thermal couples, ensures an adequate and precise temperature, since heating the cornea above 60.degree. Celsius can cause coagulation of the cornea.

By heating the corneal stroma to about or below 60 degree C., the molecules of the cornea are loosened, and the cornea changes from a substantially solid substance to a gelatinous substance or gel-like substance. However, the corneal temperature is maintained at or below 60.degree. C., and therefore, protein denaturization does not occur as with conventional thermal coagulation. Under this system, the cornea reforms and is molded to take the shape of the inner surface 32 of the reshaping device, thereby forming the cornea into the reformed, corrected shape in an effort to provide the patient with 20/20 vision. The cornea can then cooled by applying cool or cold water, by applying air or by simply removing the heated reshaping device or the heat from the reshaping device and using the ambient air temperature. As the cornea cools, it is held by the reshaping device 20 to the preferred shape, which becomes its new permanent shape once the cornea is completely cooled and changes from its gel-like consistency to its original substantially solid consistency, as shown in FIG. 6.

Figures 7, 8:
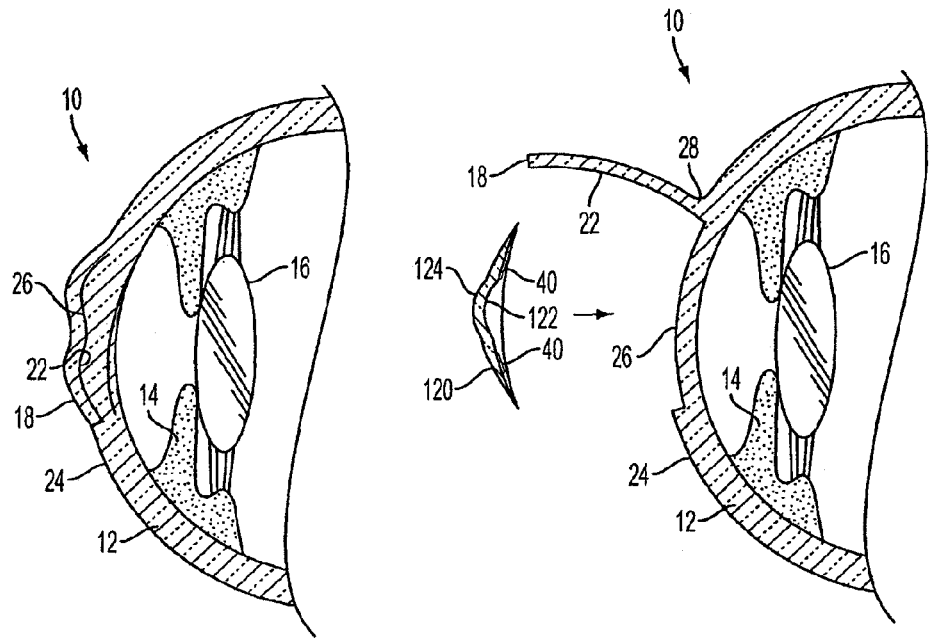
FIG. 7 is a side elevational view in cross section of the eye of FIG. 6 with the flap repositioned over the reformed exposed surface of the cornea.
FIG. 8 is a side elevational view in cross section of the eye of FIG. 2 with a reshaping device having a predetermined shape for correcting hyperopia proximate to the exposed surface of the cornea.
Figure 9:
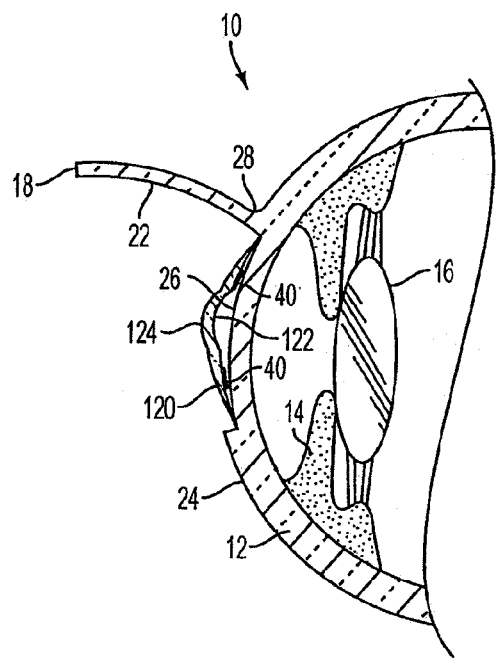
FIG. 9 is a side elevational view in cross section of the eye of FIG. 8 with the reshaping device immediately adjacent and overlying the exposed surface of the cornea.
Figure 10:
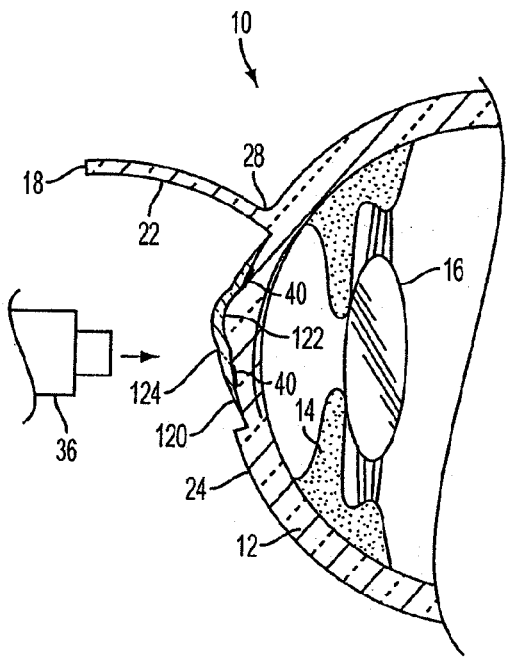
FIG. 10 is a side elevational view in cross section of the eye of FIG. 9 with a laser irradiating the surface of the cornea to cross link the cornea with the cross linked portion of the cornea conforming to the internal shape of the reshaping device.
Figure 11:
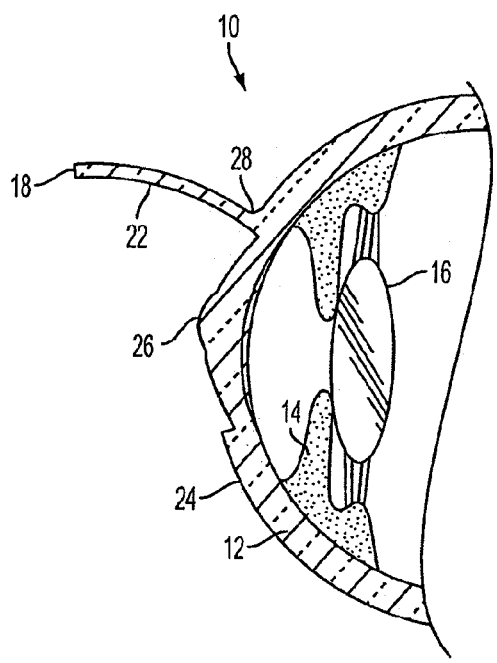
FIG. 11 is a side elevational view in cross section of the eye of FIG. 10 with the reshaping device removed and the cornea maintaining its reformed shape.
Figure 12:
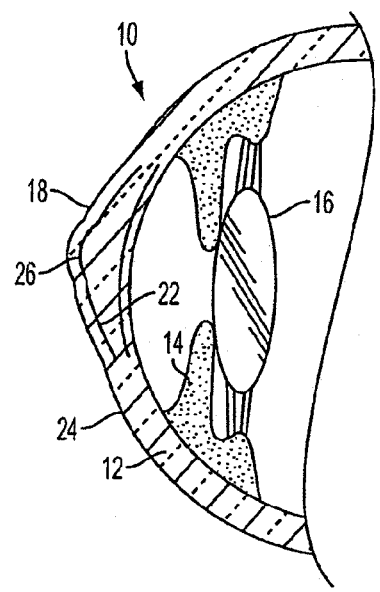
FIG. 12 is a side elevational view in cross section of the eye of FIG. 11 with the flap repositioned over the reformed exposed surface of the cornea.

The flap 18 can then replaced so that it covers or lies over the first surface 26 of the cornea 12 in a relaxed state, as seen in FIG. 7. This new permanent shape allows the cornea to properly focus light entering the eye on the retina. The refractive power of the eye is then measured to determine the extent of the correction. If necessary the method can be repeated.

A reshaping lens can be applied to the external surface of the cornea, if desired, after the flap has been replaced to maintain the proper corneal curvature or the eye can be left to heal with no additional reshaping lens being used.

Furthermore, at the end of the method, if desired, topical agents, such as an anti-inflammatory, antibiotics and/or an antiprolifrative agent, such as mitomycin or thiotepa, at very low concentrations can be used over the ablated area to prevent subsequent haze formation. The mitomycin concentration is preferably about 0.005-0.05% and more preferably about 0.02%. A short-term bandage contact lens may also be used to protect the cornea.

By reforming the cornea into the desired shape in this manner, a highly effective surgical method is formed that allows perfect or near perfect vision correction without the need to ablate any of the cornea or causing a gray to white response in the cornea of the eye.

FIGS. 8-12

As shown in FIGS. 8-12, the same general method as shown in FIGS. 1-7 can be used to correct hyperopic error in the cornea. In this method, a substantially circular convex reshaping device 120, rather than concave reshaping device 20, having a first or inner surface 122 and a second or outer surface 124, is used and placed immediately adjacent and overlying the surface 26 of the cornea. A heating element, such as a laser 36 (or any other suitable device or method), is used to heat the reshaping device, which in turn increases the temperature of the cornea to about or below 60.degree. Celsius, as described above. This heating causes the cornea to cross link and turn into a gel-like material, thereby conforming to the inner surface 122. Once the corneal surface 26 cools and is permanently or semi-permanently reformed to the inner surface of the reshaping device, the device is removed and the flap replaced, if the flap method is used. The hyperopic error is corrected and the cornea can now effectively focus light on the retina, as described above.

This method for correcting hyperopic conditions is substantially similar to the method for correcting myopic conditions. Thus, the entire method described above for correcting myopic error of the cornea applies to the correction of hyperopic error, except for the exact configuration of the reshaping device.

Figure 13:
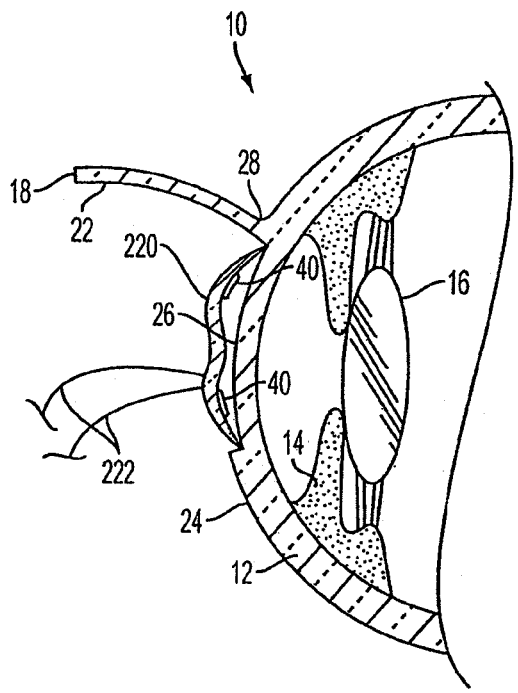
FIG. 13 is a side elevational view in cross section of the eye of FIG. 2 with a thermally conductive reshaping device having a predetermined shape immediately adjacent the exposed surface of the cornea.
Figure 14:
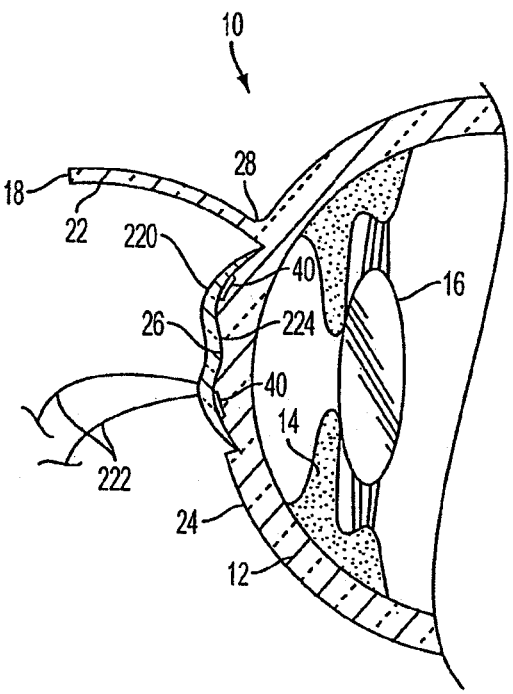
FIG. 14 is a side elevational view in cross section of the eye of FIG. 13 with the thermally conductive reshaping device administering controlled heat to the exposed surface of the cornea to cross link the cornea with the cross linked portion of the cornea conforming to the internal shape of the reshaping device.

FIGS. 13 and 14

As shown in FIGS. 13 and 14, the reshaping device can be a thermally conductive plate or reshaping device 220 that is electrically connected to a power source (not shown) using electrical wires 222. The thermally conductive plate 220 is preferably any metal or conductive material that can conduct electricity supplied by a power source (not shown) and turn the electricity into heat. Furthermore, the plate preferably is formed from a material that would allow an equal or substantially uniform distribution of heat through the plate.

This method is similar to those described above; however, the temperature of the cornea is increased using the thermocouple plate instead of a laser. As seen in FIG. 13, the plate 220 is heated to the desired temperature, preferably about or below 600 Celsius, as described above. This causes loosening of the corneal molecules or cross linking of the cornea, which allows the cornea to conform to surface 224 of plate 220, thereby permanently changing the shape of the cornea. Once the corneal surface 26 has cooled and permanently reformed to the inner surface of the thermocouple plate, the plate is removed and the flap replaced, if this method is used. The cornea can now effectively focus light on the retina, as described above.

Although, the method is shown in FIGS. 13 and 14 using a thermally conductive plate to correct myopic error, a thermally conductive plate can be used to change the shape of the cornea in any manner desired, such to correct astigmatic or hyperopic error in the cornea.

Furthermore, since this method is substantially similar to the methods described above, the description of those methods and references numerals used therein, excluding the specific lens and heating element, apply to this method.

Figure 15:
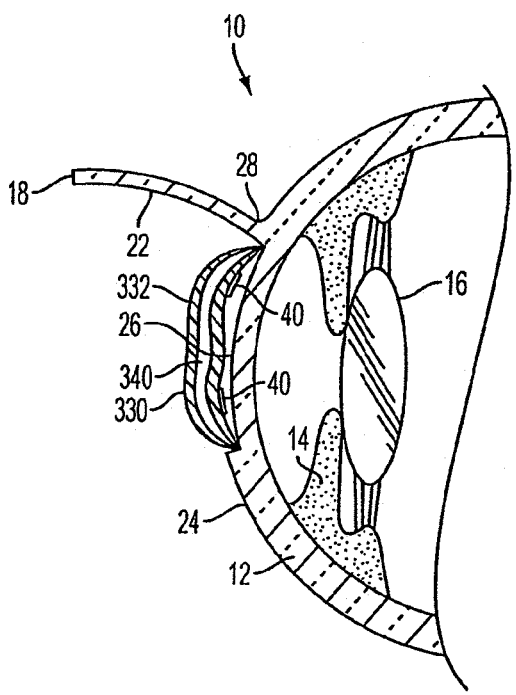
FIG. 15 is a side elevational view in cross section of the eye of FIG. 2 with a reshaping device having two passageways for irrigation and aspiration of a liquid with a predetermined temperature and having a predetermined shape immediately adjacent the exposed surface of the cornea.
Figure 16:
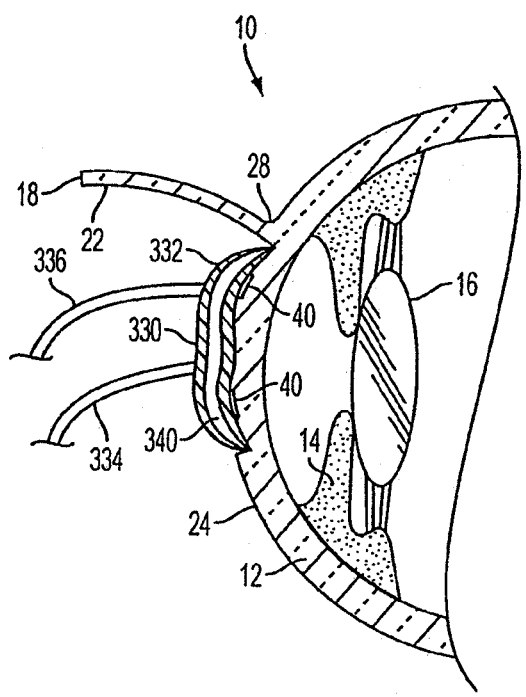
FIG. 16 is a side elevational view in cross section of the eye of FIG. 15 with the aspiration and irrigation tubes extending through the reshaping device for administering and removing liquid with a predetermined temperature to the exposed surface of the cornea to cross link the cornea with the cross linked portion of the cornea conforming to the internal shape of the reshaping device.

FIGS. 15 and 16

As shown in FIGS. 15 and 16, reshaping device 320 can be a container, i.e., hollow, with an irrigation port 330 and an aspiration port 332 providing access to interior chamber 340. Reshaping device 320 is preferably any metal or plastic that can be filled with a liquid and absorb heat and distribute the heat throughout the reshaping device in a uniform or substantially uniform manner. However, the reshaping device does not necessarily need to be metal and can be any synthetic or semi-synthetic material, such as plastic or any polymer of any material that would allow the lens to absorb the heat from the liquid and distribute the heat uniformly throughout the reshaping device.

The method of FIGS. 15-16 is similar to those described above; however, the temperature of the cornea is increased using a tube 334 that couples to the irrigation port and fills chamber 340 of the container with a liquid of a predetermined temperature, preferably about or below 60.degree. Celsius (140.degree. F.). Once filled with the liquid, the inner surface of the reshaping device would increase to the desired temperature, thereby loosening the molecules of the cornea or cross linking surface 26 of the cornea, which allows the cornea to conform to surface 324 of reshaping device 320 and results in the proper reformation of the cornea. The liquid can then be removed from the container via the aspiration tube 236, allowing the cornea to cool and permanently reform to the desired shape, as described above. Once the corneal surface 26 has cooled and permanently or semi-permanently reformed to the inner surface of the reshaping device, the reshaping device is removed and the flap replaced, if this method is used. The cornea can now effectively focus light on the retina, as described above.

Although, the method shown in FIGS. 15 and 16 uses a container to correct myopic error, this method can be used to change the shape of the cornea in any manner desired, such to correct astigmatic or hyperopic error in the cornea.

Furthermore, since this method is substantially similar to the methods described above, the description of those methods along with the reference numerals used therein, excluding the specific reshaping device and heating element, apply to this method.

FIGS. 17-20

As seen in FIGS. 17-20, a modified method does not necessarily need to be performed on the cornea, but can be performed on a separate lens or inlay 430. Inlay 430 is preferably a substantially circular polymeric or synthetic inlay or blank that has a predetermined thickness and a first side 432 and a second side 434 and is positioned under the flap adjacent second surface 26 to correct refractive error in the eye. For a more complete description of use of an inlay, see U.S. Pat. No. 6,197,019 to Peyman, the entire contents of which are herein incorporated by reference.

As described above and seen in FIGS. 18 and 19, a reshaping device 420 having a first surface 422 and a second surface 424 is placed over the inlay 430 adjacent surface 434 and heated to the appropriate temperature using a laser 36. Since the inlay is a polymer and is not formed from living cells, there is no need to keep the temperature at or about 60.degree. Celsius (140.degree. F.). The rise in temperature of the lens causes the inlay 430 to cross link or become a gelatinous material, which allows the inlay to conform to the shape of the inner surface 422 of reshaping device 420. In a similar manner to that described for the cornea above.

As seen in FIG. 20, once the reshaping device 420 is removed, the flap 18 can placed over the inlay 430. First internal surface 22 is positioned so that it overlies the second surface 434 of inlay 430 without substantial tension thereon. In other words, the flap is merely laid overtop of the inlay 430 so as to not cause undue stress or tension in the flap and possibly causing damage thereto.

It is noted that the method of FIGS. 17-20 is not limited to the first herein described method using a reshaping device and a laser, but can be used with any heating means, such as the container method and the thermally conductive plate method also described herein and any other method that would heat a reshaping device overlying the inlay to the appropriate temperature.

Additionally, this method of FIGS. 17-20 can be preformed with a lens that has a predetermined refractive index, is a blank having no refractive index or a lens that has been modified by a laser, a cryolathe or any other method known in the art to have a predetermined refractive index. For example, with a blank, the inlay can have no refractive power, the entire corrective change in the lens coming from the conformation to the inner surface of reshaping device 420 or the inlay can have refractive power with the reshaping device 420 simply modifying the refractive properties. Additionally, it is not necessary for this lens to be positioned between layers of the cornea. The lens can be positioned in any suitable position within the eye or in a position that is adjacent and external to the eye.

Although, the method shown in FIGS. 17-20 uses a lens to correct myopic error, this method can be used to change the shape of the cornea in any manner desired, such to correct astigmatic or hyperopic error in the cornea.

Furthermore, since this method is substantially similar to the methods described above, the description of those methods along with the reference numerals used therein apply to this method.

FIGS. 21-29

FIGS. 21-29 illustrate another embodiment of the present invention for correcting refractive error in the eye, wherein a laser 500, such as a short pulse laser, is used to form cavities or three dimensional portions 502 in the cornea 12 of an eye 10. A mold or lens 504 is then used to reshape the cornea to correct the refractive error in the eye.

First, as described above the refractive error in the eye is measured using wavefront technology, as is known to one of ordinary skill in the art or any other suitable method. The refractive error measurements are used to determine the appropriate shape of lens or contact 504 to best correct the error in the patient's cornea 12. Preferably, the lens or reshaping device 504 is manufactured or shaped prior to the use of the wavefront technology and is stored in a sterilized manner until that specific lens shape or size is needed. However, the information received during the measurements from the wavefront technology can be used to form the lens using a cryolathe, laser, or any other desired system, method or machine.

Preferably lens 504 is preferably clear and formed any organic, synthetic or semi-synthetic material or combination thereof, such as plastic or any polymer or any material that has pigmentation that would allow laser light to pass therethough such that laser light could heat the cornea as described herein. Lens 504 has a first surface 520 and a second surface 522. The second surface preferably is adapted to be positioned adjacent a surface of the cornea and has a predetermined curvature that will change the curvature of the cornea to correct refractive error. However, the lens does not necessarily need to be formed in this manner and can be opaque, translucent and/or formed in any manner described above or in any manner suitable for changing the curvature of the cornea.

As shown in FIG. 21, the laser 500 is preferably fired at a portion 506 of the cornea beneath or under the exterior surface 24 of the cornea, forming a predetermined pattern of cavities, which have a predetermined size and shape. In other words, the laser 500 is preferably fired at the stromal layer of the cornea. The laser is programmed to form up to about 10,000 small cavities or three dimensional aberrations 502 in the stroma of the eye. Each cavity has a diameter of about 10 microns or less to about 1 millimeter. It is noted that cavities 502 do not necessarily need to be formed in the stroma and can be formed in any portion of the cornea, such as in the Bowman's layer, the epithelial layer, or suitable portion of the eye or any combination thereof.

Laser 500 is preferably an ultra short pulse laser, such as a femto, pico, or attosecond laser; but may be any light emitting device suitable for creating cavities 502. The ultrashort pulse laser 500 is positioned in front of the eye and focuses the laser beam in the cornea 12 at the desired depth for creating multiple cavities. Ultra short pulse lasers are desired since they are capable of ablating or vaporizing corneal tissue beneath the surface of the cornea without disrupting, damaging or affecting the surface of the cornea. Additionally, ultra short pulse lasers are high precision lasers that require less energy than conventional lasers to cut tissue and do not create "shock waves" that can damage surrounding structures. Cuts or ablation performed using ultra short pulse lasers can have very high surface quality with accuracy better than 10 microns, resulting in more precise cuts than those made with mechanical devices or other lasers. This type of accuracy results in less risks and complications than the procedures using other lasers or mechanical devices. However, it is noted that the cavities 502 can be formed by any manner or device desired.

As shown in FIGS. 22-24, cavities 502 can form various configurations or patterns. For example, the cavities can form a substantially circular pattern (FIG. 22), a substantially ring-shaped pattern (FIG. 23), or a pattern that is offset from the main optical axis (FIG. 24). Each specific configuration is particularly useful for correcting a specific vision problem in the eye. For example, a substantially circular pattern facilitates correction of myopia and hyperopia, a substantially ringed shaped pattern facilitates correction of presbyopia and a pattern offset from the main optical axis facilitates correction of astigmatism. It is noted that these patterns and configurations are exemplary purposes only and the cavities can be formed in any suitable configuration for correcting myopia, hyperopia and/or astigmatism or any other refractive error in the eye.

As shown in FIG. 25 a photosensitizer or an ultraviolet absorbing compound 508 can be applied to the surface of the cornea 24 using a device or applicator 510 or any other suitable method or device. Additionally, the cross linker (i.e., the photosensitizer) can be applied also to a cross linkable material such as a corneal inlay made out of collagen or other organic, synthetic or semisynthetic material. The material can then cross linked after the reshaping device is applied. The photosensitizer can be applied to the entire cornea or merely to specific areas and can absorb ultraviolet or near ultraviolet radiation to help facilitate or create cross-linking of collagen and hold the corneal structure into the new reformed shape. A suitable material for photosensitizing the cornea is riboflavin. Additionally, photosensitizer 508 is preferably a liquid or gel that is capable of initiating or catalyzing the energy from the laser 500; however, the photosensitizer can be any suitable substance or have any suitable consistency. Furthermore, the initiator does not necessarily need to be a photosensitizer and can be any suitable substance that facilitates formation of the cavities or reduces the heat and/or energy required to form the cavities 502.

Once the photosensitizer is applied and allowed to spread through or penetrate to the corneal stroma (or other desired portion of the eye), lens or reshaping device 504 is positioned immediately adjacent the external corneal surface, as shown in FIGS. 26 and 27. Reshaping device second surface 522 which has a predetermined curvature is preferably positioned immediately adjacent the external surface of the cornea, overlying all or substantially all of the cavities 502; however, it is noted that it is not necessary for the reshaping device to overlie all or substantially all of the cavities 502 and can overlie only a portion of the cavities 502, if desired or on the exposed surface of the cornea. The reshaping device 504 is substantially similar to the embodiments described above and any description thereof is application to the present embodiment, including the use of thermal couples 505.

As shown in FIG. 28, laser or light emitting device 512 is aimed and fired at the corneal stroma, at or approximately at the portion of the cornea in which the cavities 502 are formed. Laser 512 can be the same laser, or a substantially similar laser, as laser 500, it can be any device capable of emitting ultraviolet light or near ultraviolet red radiation or laser 512 can be any suitable laser or light emitter. The laser beam L (preferably combined with the reaction from photosensitizer 508) then heats the corneal stroma to above body temperature and below a temperature at which coagulation occurs, preferably at about 60.degree. C., and preferably to between about 45.degree. C.–50.degree. C. The preferred temperatures allow or facilitate cross-linking of the collagen cells in the eye, so that the cornea can be reshaped more easily. As with the embodiments described above, the temperature can be controlled using the thermal couples and a suitable computer control system or manually. The light emitting device can also cross link the cornea without heat formation and without prior cavity formation.

Additionally, it is noted that the laser can heat the reshaping device, which in turn heats the cornea, or the cornea can be heated in any manner described herein.

By heating the corneal stroma to about or below 60.degree. C., the molecules of the cornea are loosened, and the cornea is cross linked, in a manner substantially similar to that described above. However, the corneal temperature is maintained at or below 60.degree. C., and therefore, protein denaturization does not occur as with conventional thermal coagulation. Since the heated portion of the cornea is now cross linked, the cornea reforms and is molded to take the shape of the inner surface of reshaping device 504, thereby forming the cornea into the reformed, corrected shape in an effort to provide the patient with 20/20 vision. The cornea can then cooled by applying cool or cold water, by applying air, by letting the reshaping device 504 cool through time or by simply removing the heated reshaping device or the heat from the reshaping device and using the ambient air temperature.

Figure 29:
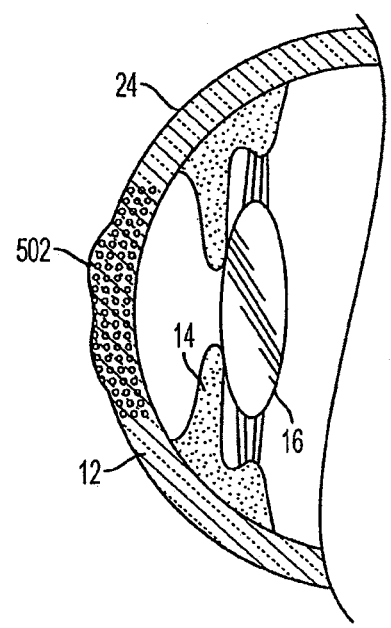
FIG. 29 is a side elevational view in cross section of the eye of FIG. 28 after the reshaping device has been removed.
Figure 33:
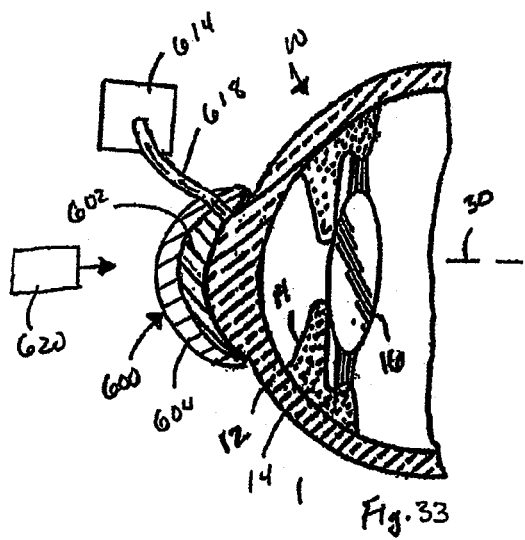
FIG. 33 a side view in section of the device of FIG. 32 with suction device holding the cornea to the internal shape of the device and a laser irradiating the reshaping device to cross link the cornea.

Preferably, as the cornea cools, it is held by the reshaping device 504 to the preferred shape, which becomes its new permanent shape once the cornea is completely cooled and changes to its original substantially solid consistency, as shown in FIG. 29.

Preferably, the reshaping device 504 is transparent as described above, thus allowing the patient to see while the reshaping device is still on the external surface of the eye. In other words, as the cornea cools, the reshaping device 504 acts as a contact lens, if desired.

Figure 3:
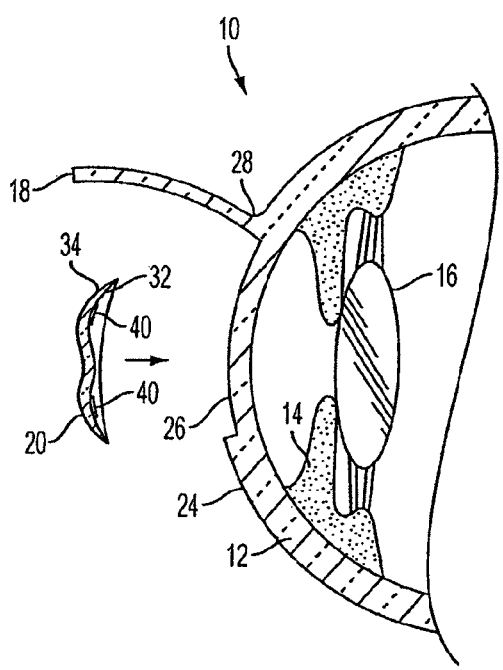
FIG. 3 is a side elevational view in cross section of the eye of FIG. 2 with a reshaping device having a predetermined shape for correcting myopia proximate to the exposed surface of the cornea.

It is noted that reshaping device does not necessarily need to be applied to the external surface of the cornea and can be positioned directly on the Bowman's layer, directly on the corneal stroma or any other suitable portion of the cornea. This positioning can be achieved by forming a flap that would expose the desired portion of the internal structure of the cornea. As described herein the flap can be a Lasik type flap (i.e., attached to the cornea at the periphery—see. FIG. 3), or it can be a flap that is attached at a central portion of the cornea (i.e., along the main optical axis), the flap can be completely removed, or the internal structure of the cornea can be exposed in any other suitable manner.

FIGS. 30-34 illustrate a device for reshaping the cornea 600 according to another embodiment of the present invention. Device 600 preferably has two portions, a first layer or portion 602 and a second layer or portion 604. However, it is noted that device 600 can be formed from one layer or portion (as described above) or multiple layers or portion, if desired.

First portion 602 has a first surface 606 that is adapted to be positioned adjacent a surface of the cornea and a second surface 608. First portion is preferably formed form a ceramic material or a polymer or another suitable material, such that the cornea of the eye is insulated from direct contact with second portion 604. Such insulation can reduce the risk of damaging, burning and/or scarring of the cornea.

Second portion 604 is preferably formed of a heat or electrically conducting material, such as metal or any material described above or any other suitable material. Portion 604 has a first surface 610 positioned substantially adjacent second surface of first portion 602 and a second surface 612 generally exposed and facing away from the patient.

The first and second portions generally have substantially the same shape and approximate thickness and second portion 604 preferably overlies first portion 602. Preferably, both the first and second portions are substantially circular or substantially ring-shaped but can be any suitable size or configuration to change the refractive properties of the eye in any desired manner or any suitable shape, In other words, the configuration of device 600 can be any suitable configuration to alter the refractive properties of the eye and correct for myopia, hyperopia, presbyopia, astigmatism or any other disorder.

The device shape can be substantially circular, substantially ring shaped, having an arcuate configuration (spanning from about 1 degree to about or less than 360 degrees) or any other configuration that could be positioned on a surface of the cornea to alter the shape thereof. Furthermore, the second portion does not necessarily need to overlie the second portion and each portion can be orientated relative to each other in any suitable or desired manner.

The first surface 606 of first portion 602 preferably has a predetermined shape to facilitate alteration of the cornea. For example, the surface can be substantially flat or have a curvature of radius that is greater than the curvature of the cornea to correct for myopic error, the surface can have a curvature that is greater than the cornea to correct for hyperopic error or the surface can be toric to correct astigmatism. The overall shape of the heated portion or the device itself can be substantially ring-shaped to correct hyperopia or presbyopia. Preferably, the substantially ring-shaped device has an opening of about 3 mm to about 8 mm, but can have any suitably sized opening.

As described herein, device 600 can be formed from any suitable material and be heated in any suitable manner. For example, device 600 can be heated using a heating source and electrical wires, heated water, a wireless device, such as a laser, or any other suitable device or mechanism. Additionally, the cornea can be heated while device 600 is positioned thereon or both the cornea and the device can be heated simultaneously. Generally, when heating the cornea in this manner, it is heated with a laser and the device is substantially transparent; however, the cornea and/or device 600 can be heated in any suitable manner.

Furthermore, the cornea can be irradiated with a laser of a specific wavelength (e.g. 375-400 nm or higher up to 3 microns or any other suitable wavelength) that will create cross linking in the cornea to facilitate alteration of the cornea. The cornea can also be altered using any type of suitable laser wavelength and heating, as described herein. The light can be circular, semicircular doughnut shaped or any other shape applied to the cornea for cross linking with or without a cross linker In one embodiment, the heating device can have portions thereof heated, while the remainder of the device is not heated. For example, the device can be substantially circular and all of the device, the outer periphery of the device the center portion of the device or any suitable portion of the device can be heated. Such selective heating allows specific portions of the device to be heated, thus transferring the heat to only select areas of the cornea to alter the refractive properties of the eye in a specific predetermined manner.

For example, a laser can be aimed and fired at only a portion of the device, the device can be wired such that electrical current can be applied to specific portions thereof, or specific portions of the device can be heated in other suitable wireless manners or in any desired manner. The heating of the cornea cross links the cornea and allows the overall shape of the cornea to be altered, as described herein.

Generally, pressure is applied to the device facilitating change of the surface of the cornea. Pressure can be applied by hand or by a tool. The pressure can be applied automatically by a means or device configured or programmed to apply a predetermined amount of suitable pressure.

Figure 34:
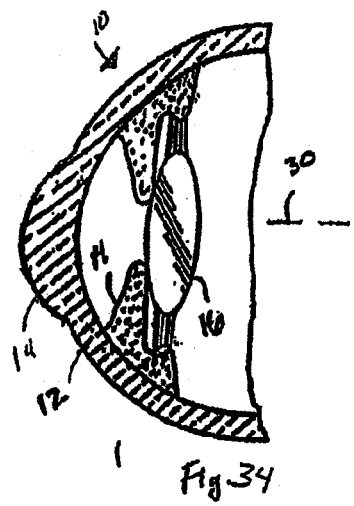
FIG. 34 a side view in section of the eye of FIG. 33 with the device removed and the cornea maintaining its reformed shape.

As shown in FIGS. 31-34, facilitating corneal change can also be achieved by using device 614 to form a vacuum between surface 606 of the device and the surface 14 of the cornea 12. For example, a small opening 616 can be formed from the second surface of the second portion of the device to the first surface of the first portion of the device. A tube 618 coupled to the device 614 for creating the suction can be coupled (or permanently affixed) to the passage, such that a vacuum or a reduced area of pressure is formed between the device 600 and cornea. Thus the cornea conforms to the predetermined shape of the first surface of the first portion of the device, a shown in FIG. 33. Simultaneously or substantially simultaneously, a laser 620 (or any other heating device described herein) heats a portion of the device 600 to facilitate altering the surface of the cornea as described above. Once the device is removed the cornea remains in the desired configuration, as shown in FIG. 34.

Suction can also be applied to the cornea using a device similar to the device in a microkeratome that creates suction to facilitate forming a LASIK style flap. A portion of the cornea can have suction applied thereto, and the mold device can be simultaneously applied to this portion or another portion of the cornea.

Furthermore, this method and device can be used in a substantially similar manner to the methods described above, the description of those methods along with the reference numerals used therein apply to this method. For example, the embodiment of FIG. 30 can be used with or without a laser forming cavities, with or without a photosensitizer, such as riboflavin, under a flap or on the surface of the cornea or any of the other methods and devices described above. Generally, the wavelength that activates the photo sensitizer is different than the wavelength to cross link the cornea; however, the any suitable wavelength can be used for either or both of the cross linking and activation of the photosensitizer.

EXAMPLE

Figure 35:
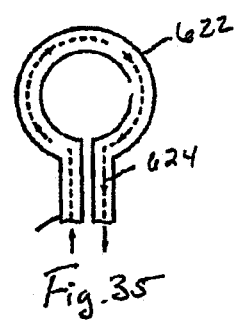
FIG. 35 is a top view of another embodiment of the present invention.

The herein described invention was performed on ten (10) eyes received from the eye bank. The device used was a copper tube 622 (FIG. 35) having a diameter of about 0.8 mm. The tube was shaped generally into a circle and positioned adjacent the external surface of the cornea. The tube can be shape as shown in FIG. 35, as a complete unitary circle with an entrance and an exit tube positioned in any suitable position relative to each other or the circle, be shaped in an arc having spanning less than 360 degrees or in any other suitable manner. Heated water 624 was passed through the tube at approximately 55 degrees Celsius. The tube made a substantially permanent indentation in the cornea, thus increasing the curvature thereof. No clouding of the cornea, damage to the corneal structure or cell death was observed and the indentation or curvature change was found to be stable.

The preferred temperature range is above body temperature and below 60 degrees C., and more preferably between about 47 degrees C. and 55 degrees C. Preferably, the cornea is heated for about 4 minutes to about 7 minutes, but can be heated to any suitable temperature for any suitable time period. Higher temperature generally requires less time of application of the device.

The amount of correction of presbyopia can be altered by changing the cross sectional diameter of the tube. For example, the smaller the diameter the less the correction and the larger the diameter the greater the correction of presbyopia. Preferably the diameter of the tube is between about 0.5 mm and 1.5 mm, but can be any suitable diameter.

In another embodiment, tube 622 or device 600 can be formed from glass of another transparent or translucent material and laser light can be transmitted through the tube to cross link the cornea (e.g., fiber optics).

Any of the above described devices can be heated themselves to alter the cornea, can work in conjunction with a device that heats the cornea directly or both the device and the cornea can be heated. Additionally, both a laser that irradiates the cornea with a cross linking wavelength and heating the cornea can be used simultaneously or in succession or any combination of these procedures, including the use of a photosensitizer can be used.

In another embodiment, cross linking of the collagen of the cornea and shrinkage or controlled altering of the cornea can be achieved with a cross linker or cross linking substance (e.g. Riboflavin). Preferably, the cross linker has between about 0.1% Riboflavin to about 100% Riboflavin or any specific range therein. This procedure is preferable performed using a device or means for emitting ultraviolet rays at the cornea. The modification or alteration of the cornea is then performed using a mold or device that has a predetermined configuration as described above.

The procedure using the cross linking substance can be used with the controlled heat methods described above, with ultraviolet rays or both or neither. Additionally, this procedure can be used to correct any and all refractive errors. For example, this method can be used to correct myopia, hyperopia, astigmatism, presbyopia and/or any other error.

The chemical cross linker (i.e., using a cross linking substance) can be performed before, simultaneous or after heat cross linking, if heat is used. Although not necessary, using both heat and the cross linking substance, will allow each to work synergistically with the other and reduce the time and temperature of cross linking needed.

When undertaking the procedure, the Photosensitizes or cross linkers can be applied to the corneal epithelium or the epithelium can be removed or the cross linkers can be applied to any exposed portion of the eye, such as the Bowman's Layer or the stroma. For example, a LASIK style flap or an epithelial style flap can be formed and the cross linker can be applied thereto. In is noted that a flap does not need to be formed and a portion of the cornea can be exposed in any desired manner.

The ultraviolet radiation or rays (when applied) are preferably between about 370 nanometers and about 380 nanometers. The radiation is preferably about 3 mW or more as needed and emanates from a device at about 3 cm distance from the cornea for about 30 minutes or less. However, the ultraviolet radiation can be applied at any suitable distance, time or wavelength.

Preferably the device for reshaping the eye has any suitable configuration, as described above, for altering correcting refractive error. Preferably, the device is positioned on the exterior or the eye (i.e., on the epithelial layer). However, as with the cross linking substance, the device can be positioned on any exposed surface of the cornea, such as the Bowman's Layer or the stromal layer. Each of these layers or any other suitable layer of the cornea can be exposed using a pocket, flap, ablation or by removing portions of the cornea or in any suitable manner.

By virtue of the predetermined configuration of the device, the device alters the shape of the cornea, thus correcting the refractive error. The device can be preformed to correct any known refractive problem or alter the refractive properties of the cornea in any desired manner.

If desired, a means for applying pressure can be used to apply pressure to the device and thus help facilitate the altering of the corneal surface. The means can be any suitable portion of the person performing the procedure or any suitable tool than could attach or merely abut the outer surface of the device.

Preferably a control system, such as a computer, monitors and controls each of the aspects of the system, including but not limited to applying heat, ultraviolet radiation, applying the cross linker, and applying pressure to the device; however, it is noted that it is not necessary for a computer control system to monitor and control each of these systems and steps and can monitor and/or control any number of the systems and steps Further, it is not necessary to even use a computer control system.

This procedure or any of the procedures described herein can be used alone, or in conjunction with, simultaneously with, before or after any other procedure, method or device that would alter, correct or enhance the refractive properties of the eye.

Implantation of polymeric material is a common procedure to replace or improvement of the function of various organs. It is known that all implants are encapsulated by fibrous or fibrovascular tissue. Though this encapsulation can be beneficial, often it can lead to complications of gradual expulsion of the implants or produce considerable cloudiness of the surrounding proliferating fibrous tissue e.g. in the cornea.

To our knowledge except for the use of immunosuppressive agents which have significant side effects no other method is available to prevent or reduce the intensity of this process.

While this application describes the use of a new methodology to reduce the chance of encapsulation in an animal cornea when an organic or synthetic material is implanted the technology is not limited to this area it can be applied also to glaucoma shunt, cosmetically or functionally used implants or prevention of vessel restenosis after stent placement.

FIGS. 40a-e illustrate another embodiment of the present invention. In particular, the present embodiment includes cross linking tissue, specifically collagen and other proteins surrounding an implant 800, to make the tissue less vulnerable to enzymatic degradation and change; thereby making the cornea 802 less likely to be invaded by various migrating cells, such as leucocytes, macrophages, fibroblasts and blood vessels endothelial cells. These cells subsequently build the basis for gray-whitish discoloration along with vascular components seen in encapsulated implants.

Figure 36A:
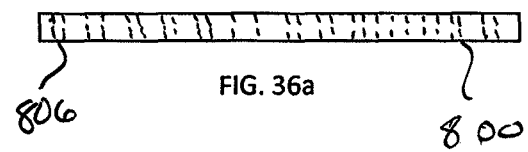
FIGS. 36a-h show membrane characteristics and exemplary positions in the cornea.
Figure 36B:
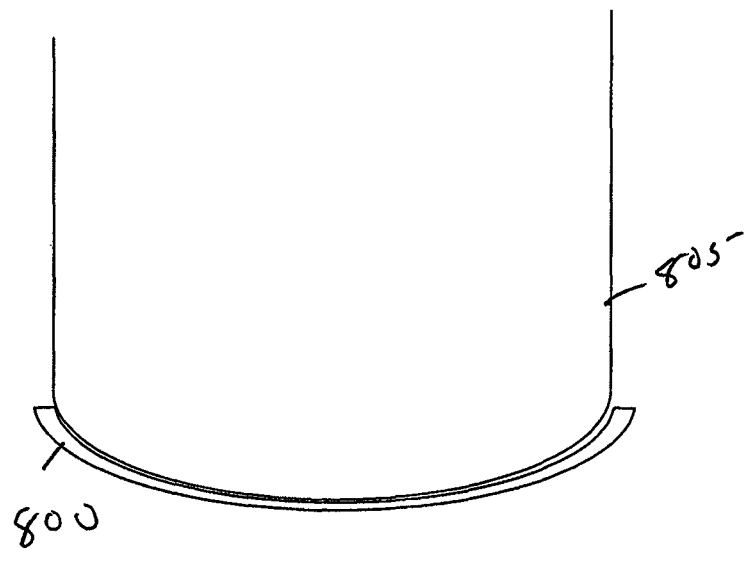
Figure 36C:
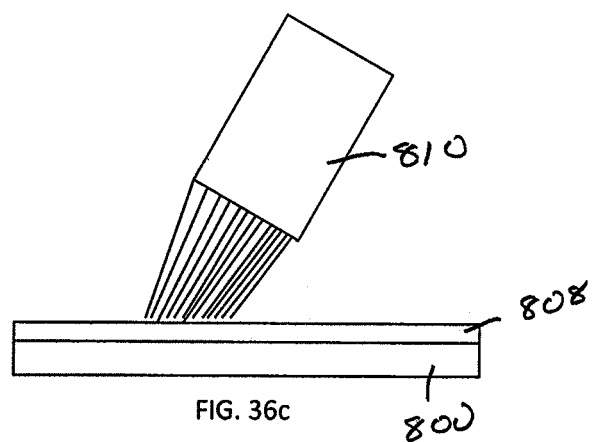
Figure 36D:
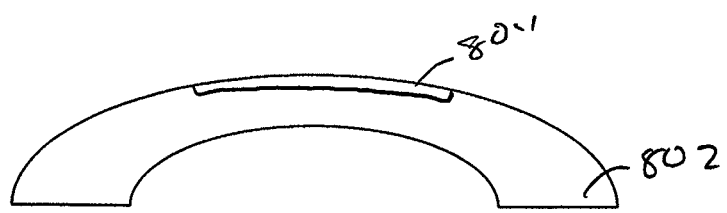
Figure 36E:
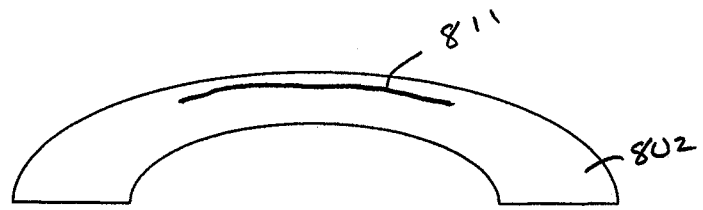
Figure 36F:
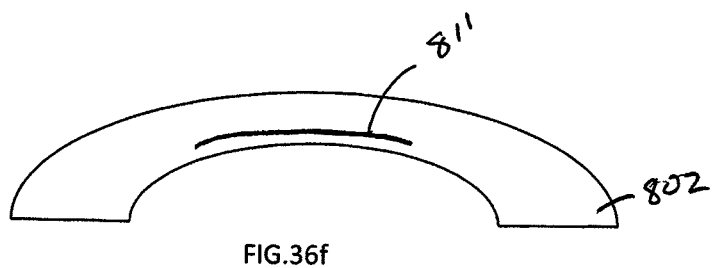
Figure 36G:
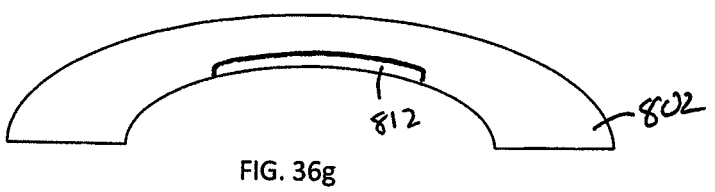
Figure 36H:
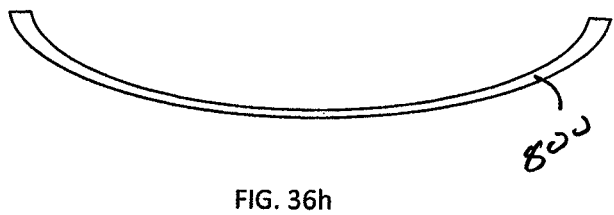
Figure 37A:
FIGS. 37a-d show formation of an internal pocket in the cornea and injection of a liquid polymer followed by cross linking.
Figure 37B:
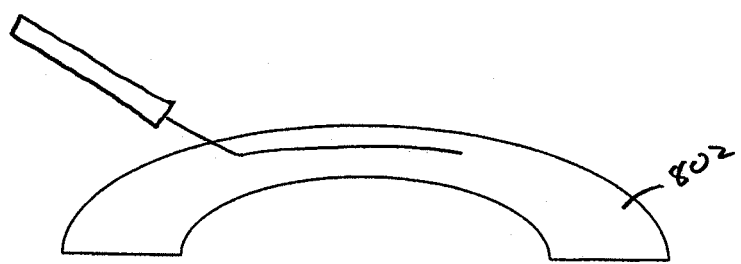
Figure 37C:
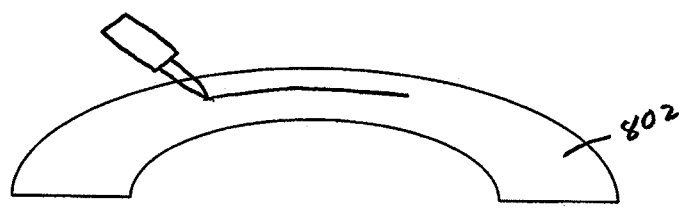
Figure 37D:
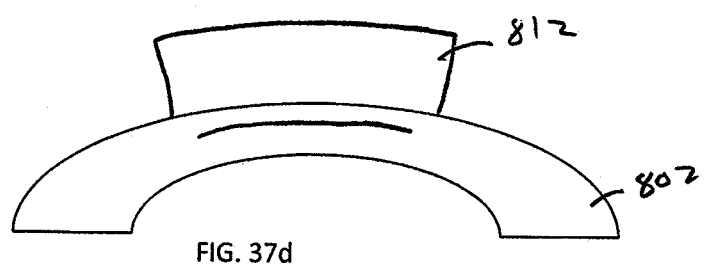

The implant 800 is generally implanted under a corneal flap 804. Thus, the implant may be surrounded completely by the corneal tissue or partially exposed out to a side surface or to the inside limited by the anterior chamber of the eye. The implant can be an organic or synthetic, hydrophilic, hydrophobic polymer, and can have minute (<2 micron) holes 806 therein for transport of fluid thereacross. The implant 800 can have a thickness of <1-500 micron or >, and can have a cross linking substance in it. The implant can be shaped into a predetermined configuration using a toll 805, as shown in FIGS. 36b and 36h.

FIGS. 37 and 38 show flap 804, which can be circular or any shape involving 20-360 degrees of the cornea. The flap diameter can be 2 mm-12 mm and the flap can have a thickness of 50 microns to >400 microns. To form the flap, a Micro-keratome or a Femto-second laser, etc. (before or after cross linking) can be used to create the incision in the cornea of any desired shape circular or doughnut or sectorial. The flap can be made in any portion of the cornea desired. For example, see FIGS. 36d-g in which the flap 804, or an incision 811 can be made in the stroma, the epithelial, near the surface of the corena, or near the anterior chamber. Moreover, as illustrated in FIGS. 36d-g, the epithelial, at the surface of the cornea or at the anterior chamber (see 812) can be removed.

Polymeric material 808, such as gel nail etc, can be injected or painted under the corneal flap (e.g., using brush 810), as a very thin layer of the cornea is compressed from outside using a contact lens or sclera lens 812 having a desired inside curvature to correct the refractive error of the cornea and subsequently cross linked. During the cross linking this semi-liquid film of polymer spreads uniformly when compressed from outside with contact lens 812 and creates the desired curvature which remains stable after the cross linking process is finished (as is done with the nail gel). This can also serve as a mechanical support to a weak cornea, etc. (when the implant is hardened during the cross linking with UV light) as in corneal ectasia seen in keratoconus patients or after LASIK surgery, etc. It is important to note that the polymer 808 per se (i.e., by itself) will not necessarily have a refractive surface and cannot correct refractive errors of the eye unless it is shaped by the compression effect exerted on the cornea by a specific contact lens 812 which has a specific curvature to correct the refractive error after the implant is hardened. If the polymer 808 and the cornea 802 were not cross linked in this position one would not achieve any predictable corrective or supportive effect.

Figure 38A:
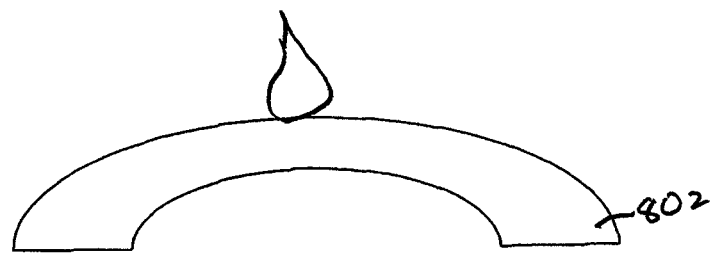
FIGS. 38a-g illustrates a surgical technique under a corneal flap, cross linking and reshaping with a contact lens.
Figure 38B:
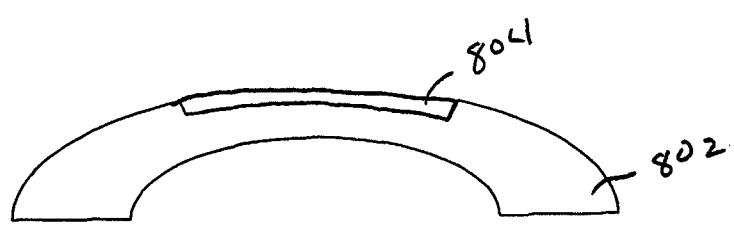
Figure 38C:
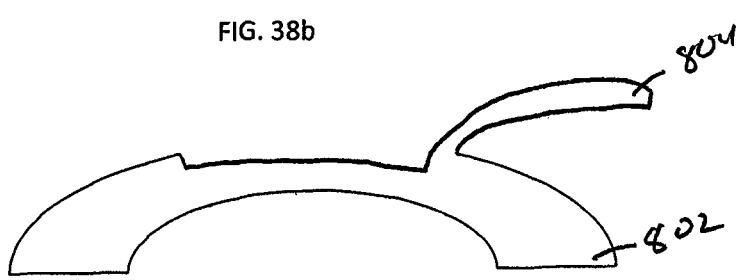
Figure 38D:
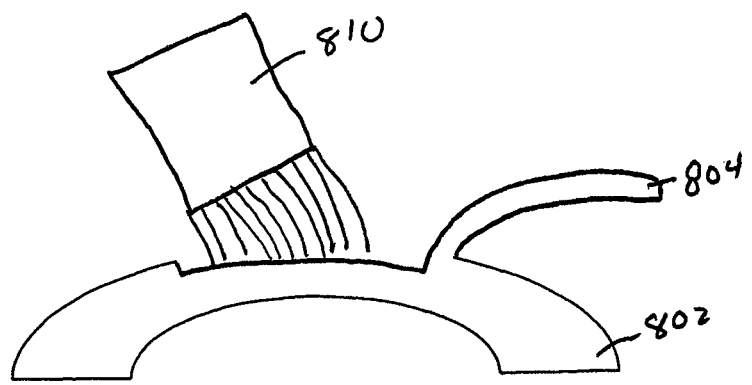
Figure 38E:
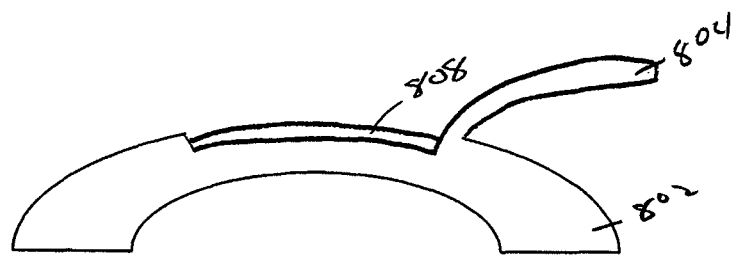
Figure 38F:
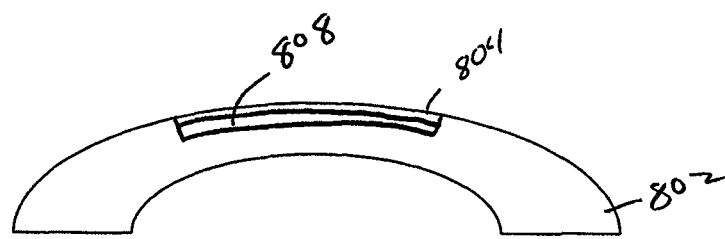
Figure 38G:
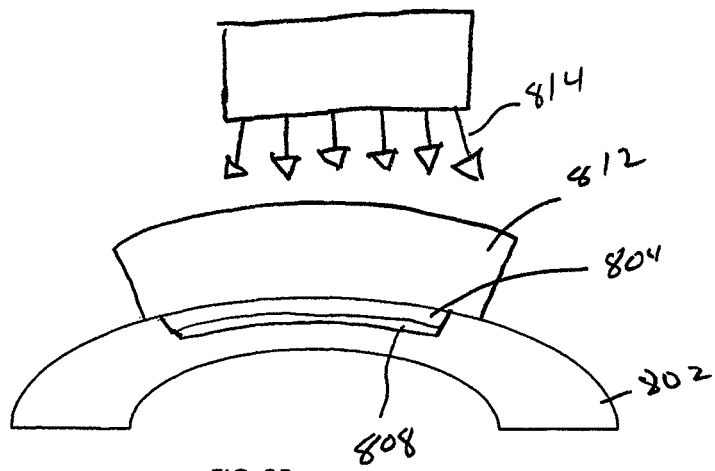
Figure 39A:
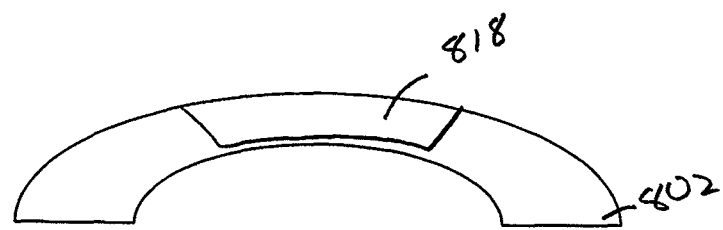
FIGS. 39a-f show implantation by leaving one surface exposed.
Figure 39B:
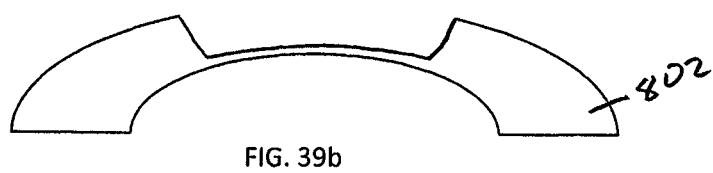
Figure 39C:
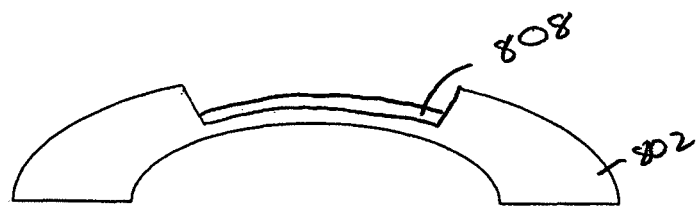
Figure 39D:
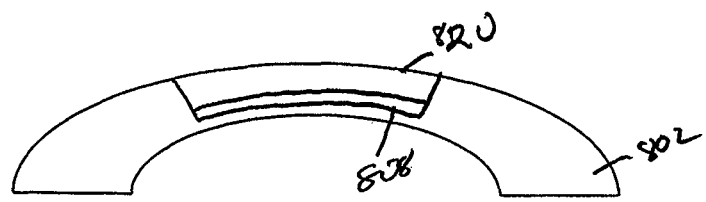
Figure 39E:
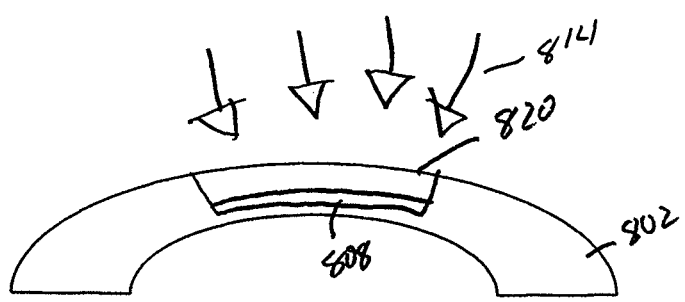
Figure 39F:
Figure 40A:
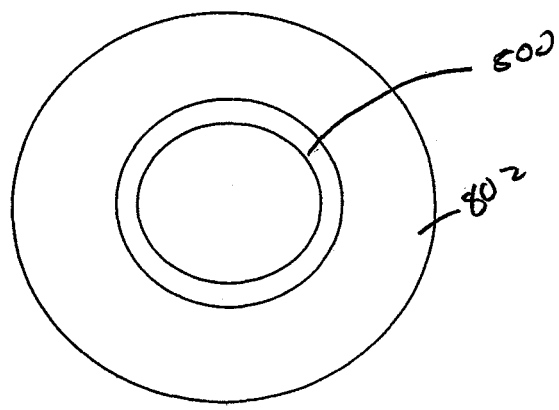
FIGS. 40a-e illustrate various embodiments of a implant inserted into the cornea.
Figure 40B:
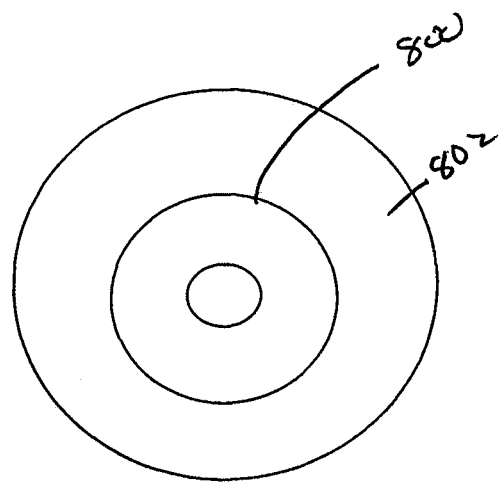
Figure 40C:
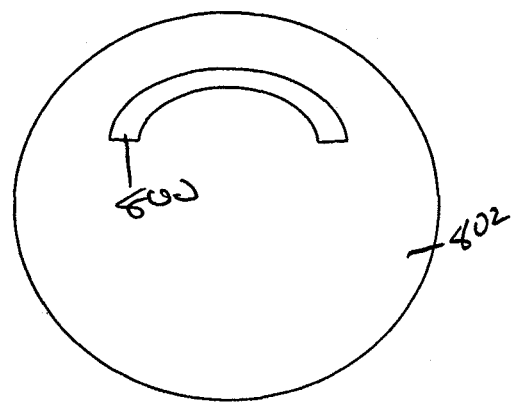
Figure 40D:
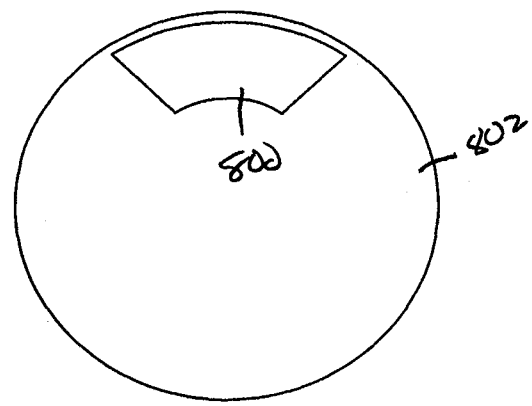
Figure 40E:
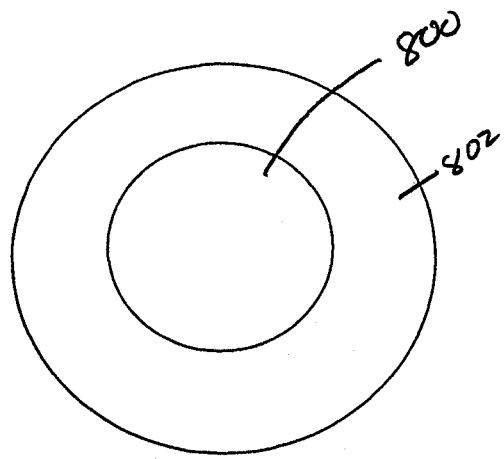

Cross linking (see FIG. 38a) is achieved by various processes, such as using Riboflavin plus subsequent radiation with near UV light 814 to activate cross linkers (see FIGS. 38g and 39e). Other cross linking methods include radiation, heat, gluthar-aldehyde and other solutions, such as low carbon sugars, etc. The tissue in which the implant is placed can be cross linked ahead of implantation or after implantation. The implant can have a cross linker coated or incorporated in it which can leak in the surrounding tissue then subjected to radiation. Preferably, the cross linking includes some tissue outside the perimeter of the implant.

Cross linking of the corneal collagen can be achieved with a cross linker or cross linking substance (e.g. Riboflavin). Preferably, the cross linker has between about 0.1% Riboflavin to about 100% Riboflavin or any specific range therein. This procedure is preferable performed using a device or means for emitting ultraviolet rays at the cornea.

When undertaking the procedure, the Photosensitizes or cross linkers can be applied to the corneal epithelium or the epithelium can be removed or the cross linkers can be applied to any exposed portion of the eye, such as the Bowman's Layer or the stroma. For example, a corneal flap or an epithelial style flap can be formed and the cross linker can be applied thereto.

The ultraviolet radiation or rays (when applied) are preferably between about 370 nanometers and about 380 nanometers. The radiation is preferably about 3 mW or more as needed and emanates from a device positioned at about 3 cm from the cornea for about 30 minutes or less. However, the ultraviolet radiation can be applied at any suitable distance, time or wavelength. The standard way of cross linking the cornea does not provide a complete stability, since the cornea does not change the refractive power of the cornea significantly.

Attempts to reshape the cornea by external means during the cross linking the device for reshaping the eye has been successful. Although the use of corneal inlays has been described, these have been often fraught with encapsulation and corneal cloudiness. These implants have tried to change the curvature of the front surface of the cornea by acting like an optical lens having a surface with defined surface and curvature (convex or concave etc.) to create the desired change on the surface of the cornea. This implant does not provide any substantial stability to the cornea and can also be rejected by the corneal tissue. Therefore, there is a need to provide a means of providing internal stability to the cornea using a thin flat membrane-like implant that has little or no refractive surface but can be significantly hardened after cross linking without its surface swelling (increase in thickness or decrease in thickness). However, a hardness can be achieved that is needed after cross linking and a new curvature can be adopted before the cornea is cross linked. If pressed on during the hardening process, the thin flat membrane-like implant can assume a refractive curvature (similarly to gel nail which is painted over the nail that assumes the nail curvature when it hardens). This new implant can be applied on the tissue or under the tissue (e.g., a corneal flap) like a paint over or can be implanted as a flexible transparent membrane inside the tissue then hardened or cross linked with UV. radiation. (FIG. 36a-h). The membrane can have a cross linker substance thereon to harden during the radiation. The membrane may have the same cross linker that is used for the tissue and the implant.

Initially, the implant has no curvature; however, the implant can change the refractive power of the cornea if it is pressed against a curved surface during the cross linking and hardens in that position. When the implant hardens, it provides a "back bone" for the cornea and prevents corneal ectasia. A cross linking substance is applied as described above to the exposed corneal stroma or under the corneal flap.

In another embodiment, shown in FIGS. 39*a-f*, if desired, and preferably after the implantation and cross linking, the remaining corneal thickness under 816 or over the implant 818 can be removed e.g. from the inside the anterior chamber through a small incision using an angulated, knife, scissors, or laser to cut the tissue which is subsequently removed with a fine forceps under viscoelastic material. This technique can create a clear window to outside world. Additionally, as shown in FIGS. 39*e* and *f,* the remaining cornea or a donor portion 820 from an eye bank can be positioned in the opening created by removal of the remaining corneal thickness.

Embodiments of FIGS. 41*a-f*

It is known to one of ordinary skill in the art, that the normal corneal thickness is about 490-560 microns. Generally, thin corneas are found often in patients who have high myopia (i.e., near sightedness). Such thin corneas, i.e., having a thickness of <480 microns, are not candidates for modern refractive surgery using an excimer laser or any tissue removal for the correction of refractive errors. That is, ablation of these corneas affects biomechanics of the cornea, leading to out-bulging of the cornea, which often requires a corneal transplant. Cross linking of the cornea has been recently advocated to correct the refractive problems of the eyes having these types of corneas (e.g., by the present inventor) for advanced corneal ectasia, such as in Keratoconous to stabilize the condition. However, no method exists to perform refractive surgery on thin corneas. The corneal ablation in these patients generally will lead to further thinning of the cornea, reduced stability of the cornea, and possible corneal perforation.

The present embodiment of this invention, as shown in FIGS. 41*a-f* is a method for correcting refractive error in patients with thin corneas, e.g., <500 microns thick. Except for glasses, contact lenses or implantation of a corrective lens inside the eye, there is no known method to correct the refractive errors of these types of patients.

This embodiment has the following advantageous: 1) prevents corneal ektasia in eyes with thin cornea undergoing laser ablative surgery to correct refractive error of the eye; 2) reduces the sensation of burning of the cornea after surface ablation, since the corneal sensation is slightly reduced after initial corneal cross linking done in this procedure; and 3) reduces the corneal haze response to the laser ablation when the cornea is cross linked and after a period of healing laser ablation is performed. Moreover, a cross linked cornea does not respond to injury as strongly as the normal cornea does. This lack of response makes it also possible to perform ablation of the cornea in cases of high refractive error since a normal cornea would generally create haze after such procedure.

Figure 41A:
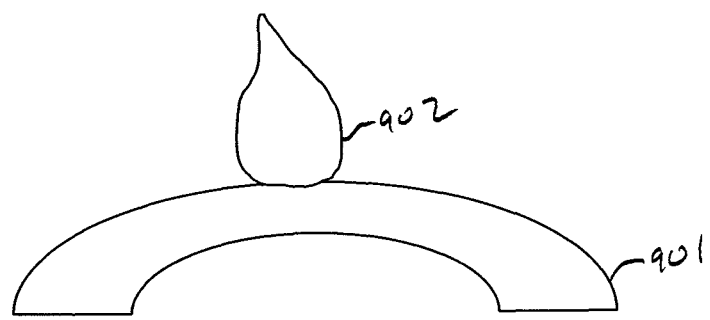
FIGS. 41a-f illustrate an embodiment which combines the use of cross linking and ablation to change the refractive properties of the eye.
Figure 41B:
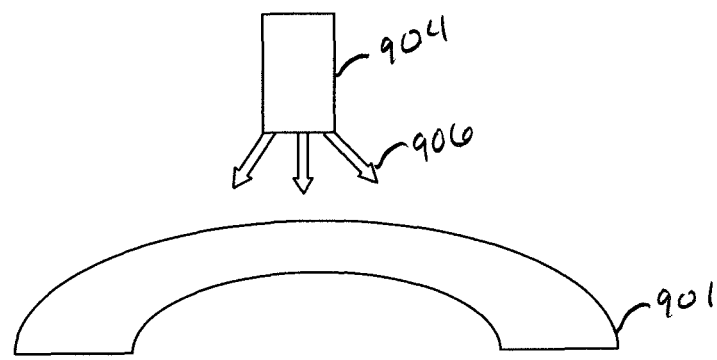

Generally, the present embodiment combines corneal cross linking with a refractive surgical procedure. More particularly, in one embodiment, the cornea is cross linked to stiffen the cornea prior correction of the refractive error followed by refractive surgery after the cornea is held, or in another embodiment, reversing the order by initially performing the refractive surgery followed by corneal cross linking within a predetermined period of time In one embodiment, as shown in FIG. 41*a*, cross linking of the cornea 901 can be achieved by at least one of various processes, such as the use of a substance 902, such as Riboflavin, and subsequent radiation with a device 904, such as a laser, which emits near UV light so as to activate cross linkers (see FIG. 41*b*). Other cross linking methods include radiation, heat, microwave, gluthar-aldehyde and other solutions such as low carbon sugars, etc. In one or more embodiments, the cornea is irradiated with at least one of near UV light, heat, and microwaves.

Preferably, the cross linker has between about 0.1% Riboflavin to about 100% Riboflavin or any other suitable range or specific percentage therein. In this embodiment, device or means 904 for emitting ultraviolet rays 906 is used, along with the position of its application. In another embodiment, the solution can be applied as a liquid suspension having nano particles of Riboflavin. Such an embodiment uses specific lenses for focusing the light.

When undertaking the procedure, the Photosensitizes or cross linkers can be applied to the corneal epithelium or the epithelium can be removed or the cross linkers can be applied to any exposed portion of the eye, such as the Bowman's Layer or the stroma. For example, a corneal flap 907 (see FIGS. 41*c* and *d*) or an epithelial flap can be formed and the cross linker can be applied to the portion of the eye that has been exposed.

The ultraviolet radiation or rays (when applied) are preferably between about 370 nanometers and about 380 nanometers. The radiation is preferably about 3 mW or more as needed and emanates from device 904 at about 3 cm distance from the cornea for about 30 minutes or less. The time of the exposure can vary depending on the light intensity, focus, and the concentration of Riboflavin. However, the ultraviolet radiation can be applied at any suitable distance, time or wavelength. Preferably, cross linking the cornea does not significantly change the refractive power of the cornea; however, if desired, cross linking can change the refractive power of the cornea to any suitable degree.

Figure 41C:
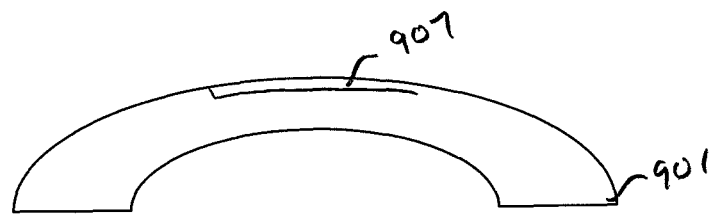
Figure 41D:
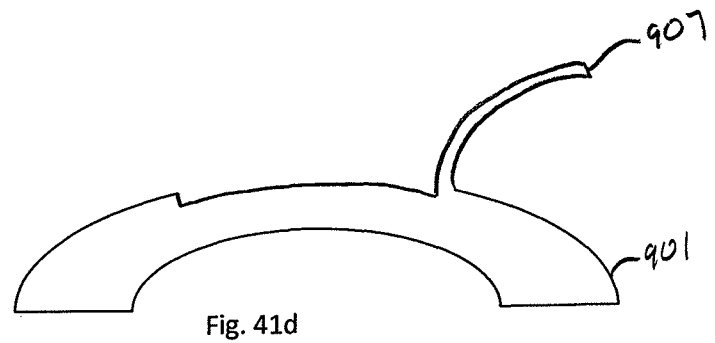
Figure 41E:
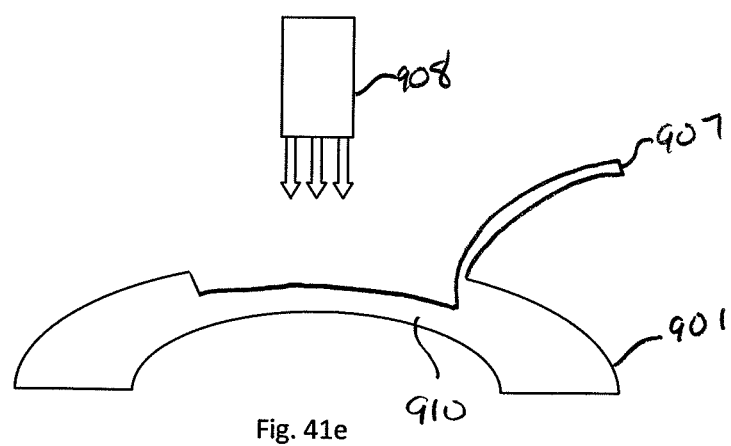

After performing the corneal cross linking and waiting a reasonable time (e.g., 1-6 weeks or more or any suitable amount of time) for the cornea to recover, the cornea 901 can be altered by a laser unit 908, such as an excimer laser, as shown in FIG. 41*e*, or other by other suitable methods. In one embodiment, the excimer laser ablates a portion of the cornea, such that a corneal portion 910 is thinner than prior to ablation. Such alteration changes the refractive properties of the cornea, thus enabling correction of vision in the eye.

Preferably, a predetermined period of waiting may allow for reduction or elimination of any photosensitizer which might still be present in the cornea after cross linking; however, the period of waiting can be any suitable period of waiting and is not necessary. Initially, prior to ablation, the refractive power of the eye is determined. This information is then transmitted to laser unit 908 to ablate the cross linked cornea. The ablation can be done intrastromally, as with LASIK (laser-assisted in situ keratomileusis), or on the surface of the cornea, as with PRK (Photorefractive keratectomy).

In particular, as shown in FIGS. 41*c-e*, a flap 907 (e.g., a stromal flap, an epithelial flap or any other suitable flap) can be formed in the cornea 901 using any known method, such as using a microkeratome (not shown). As shown in FIG. 41*d*, the flap 907 can then been moved so as to expose a portion of the cornea underlying the flap, such as the stroma surrounding the main optical axis of the eye, or any other suitable portion of the cornea. Preferably, the portion underlying the flap is an area at or surrounding the main optical axis; however, this portion can be any suitable portion of the corena. Exposing the cornea in this manner enables excimer laser 908 to irradiate the cornea so as to ablate a portion thereof, as shown in FIG. 41*e*.

Figure 41F:
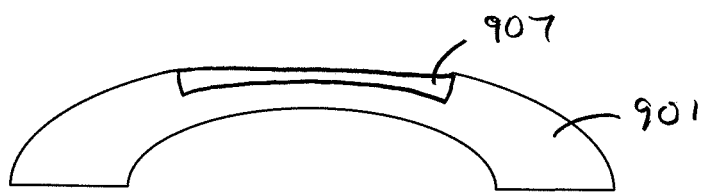

As shown in FIG. 41*f*, this procedure is effective for altering the curvature of the cornea, such that myopia, hyperopia and astigmatism or any other suitable vision problems can be corrected. Moreover, by performing the cross linker before or after ablation of the cornea (or other method altering the refractive properties of the eye) the cornea becomes stiffer, thus preventing corneal out bulging after laser ablation, since laser ablation makes a thin cornea even thinner. That is, the cross linked cornea facilitates resistance of the intraocular pressure, which pushes the cornea forward.

Additionally, post operative medications are anti-inflammatory agents, antibiotics etc., can be applied to the cornea.

This procedure or any of the procedures described herein can be used alone, or in conjunction with, simultaneously with, before or after any other procedure, method or device that would alter, correct or enhance the refractive properties of the eye. Additionally, any of the herein described embodiments can be used with any combination of the other embodiments.

While various advantageous embodiments have been chosen to illustrate the invention, it will be understood by those skilled in the art that various changes and modifications can be made therein without departing from the scope of the invention as defined in the appended claims.

What is claimed is:

1. A method of altering the refractive properties of the eye, said method comprising:
    forming a flap in a thin cornea that has a thickness of less than 480 microns, so as to expose one of the stroma and the Bowman's Layer of an eye;
    after forming the flap in the thin cornea, applying a liquid suspension having nano particles of riboflavin to the one of the stroma and the Bowman's Layer of the eye, the nano particles facilitating cross linking of the one of the stroma and the Bowman's Layer of the thin cornea;
    irradiating the thin cornea with at least one of ultraviolet light and microwaves so as to activate cross linkers in the thin cornea and thereby stiffen the thin cornea and prevent corneal ectasia in the thin cornea;
    after the thin cornea has been stiffened by the activation of the cross-linkers, ablating a portion of the thin cornea underlying the flap so as to change the refractive properties of the eye; and further comprising waiting a predetermined time period after the thin cornea has been irradiated to allow for reduction or elimination of any amount of the photosensitizer that remains present in the thin cornea prior to the ablating of the thin cornea underlying the corneal flap.

2. The method of claim 1, wherein the predetermined time period is between one and six weeks.

3. A method of altering the refractive properties of the eye, said method comprising:
    forming a flap in a thin cornea of an eye so as to expose the stroma of the thin cornea underlying the flap, the thin cornea having a thickness of less than 480 microns;
    after forming the flap in the thin cornea, applying nano particles of riboflavin to the stroma of the thin cornea underlying the flap, the riboflavin facilitating cross linking of the stroma of the thin cornea;
    irradiating the thin cornea with at least one of ultraviolet light and microwaves so as to activate cross linkers in the thin cornea and thereby stiffen the thin cornea and prevent corneal ectasia in the thin cornea;
    after the thin cornea has been stiffened by the activation of the cross-linkers, ablating the stroma of the thin cornea underlying the corneal flap using an excimer laser so as to change the refractive properties of the eye;
    replacing the flap over the ablated stroma of the thin cornea, and further comprising waiting a predetermined time period after the thin cornea has been irradiated to allow for reduction or elimination of any amount of the photosensitizer that remains present in the thin cornea prior to the ablating of the stroma of the cornea underlying the corneal flap.

4. The method of claim 3, wherein the predetermined time period is between one and six weeks.

\* \* \* \* \*